United States Patent
Allef et al.

(10) Patent No.: US 9,271,908 B2
(45) Date of Patent: Mar. 1, 2016

(54) AQUEOUS HAIR AND SKIN CLEANING COMPOSITIONS COMPRISING BIOTENSIDES

(71) Applicant: Evonik Industries AG, Essen (DE)

(72) Inventors: Petra Allef, Essen (DE); Christian Hartung, Essen (DE); Martin Schilling, Bonn (DE)

(73) Assignee: EVONIK INDUSTRIES AG, Essen (DE)

( * ) Notice: Subject to any disclaimer, the term of this patent is extended or adjusted under 35 U.S.C. 154(b) by 0 days.

(21) Appl. No.: 14/368,657

(22) PCT Filed: Dec. 11, 2012

(86) PCT No.: PCT/EP2012/075024
§ 371 (c)(1),
(2) Date: Jun. 25, 2014

(87) PCT Pub. No.: WO2013/098066
PCT Pub. Date: Jul. 4, 2013

(65) Prior Publication Data
US 2014/0349902 A1    Nov. 27, 2014

(30) Foreign Application Priority Data
Dec. 28, 2011 (DE) .......................... 10 2011 090 030

(51) Int. Cl.
| | | |
|---|---|---|
| C11D 1/00 | (2006.01) |
| C11D 3/22 | (2006.01) |
| C11D 3/37 | (2006.01) |
| C11D 3/40 | (2006.01) |
| C11D 3/50 | (2006.01) |
| A61K 8/36 | (2006.01) |
| A61K 8/60 | (2006.01) |
| A61Q 5/02 | (2006.01) |
| A61Q 5/12 | (2006.01) |
| A61Q 19/10 | (2006.01) |

(52) U.S. Cl.
CPC . *A61K 8/36* (2013.01); *A61K 8/361* (2013.01); *A61K 8/602* (2013.01); *A61Q 5/02* (2013.01); *A61Q 5/12* (2013.01); *A61Q 19/10* (2013.01); *A61K 2800/10* (2013.01); *A61K 2800/72* (2013.01)

(58) Field of Classification Search
CPC ........ C11D 1/00; C11D 1/662; C11D 3/2075; C11D 3/2079; C11D 3/22; C11D 3/37; C11D 3/40; C11D 3/50; C11D 7/265; C11D 7/268; A61K 8/36; A61K 8/60; A61Q 5/02
See application file for complete search history.

(56) References Cited

U.S. PATENT DOCUMENTS

| | | | |
|---|---|---|---|
| 7,556,654 | B1 | 7/2009 | Nero |
| 7,985,722 | B2 | 7/2011 | DeSanto |
| 2010/0004472 | A1* | 1/2010 | Kitagawa et al. ............. 549/417 |
| 2011/0257116 | A1 | 10/2011 | Kitagawa et al. |
| 2012/0220464 | A1 | 8/2012 | Giessler-Blank et al. |
| 2013/0072414 | A1* | 3/2013 | Price et al. .................... 510/220 |
| 2014/0113818 | A1 | 4/2014 | Develter et al. |
| 2014/0194336 | A1 | 7/2014 | Develter et al. |

FOREIGN PATENT DOCUMENTS

| | | |
|---|---|---|
| CN | 1337439 A | 2/2002 |
| CN | 101316574 A | 12/2008 |
| DE | 2939519 A1 | 4/1980 |
| DE | 19600743 A1 | 7/1997 |
| DE | 19648439 A1 | 5/1998 |
| DE | 102005011785 A1 | 9/2006 |
| DE | 102008001788 A1 | 11/2009 |
| EP | 0499434 A1 | 8/1992 |
| EP | 1411111 A1 | 4/2004 |
| EP | 1445302 A1 | 8/2004 |
| EP | 1771148 | 1/2006 |
| EP | 1771538 | 1/2006 |
| EP | 2000124 A1 | 12/2008 |
| FR | 2740779 A1 | 5/1997 |
| FR | 2855752 A1 | 12/2004 |
| JP | 60-183032 A | 9/1985 |
| JP | 01-304034 A | 12/1989 |
| JP | 2006-070231 A | 3/2006 |
| JP | 2006-083238 A | 3/2006 |
| JP | 2006-274233 A | 10/2006 |
| JP | 2007-181789 A | 7/2007 |
| JP | 2008-062179 A | 3/2008 |
| JP | 200869075 | 3/2008 |
| JP | 2009-275145 A | 11/2009 |
| JP | 201126277 | 2/2011 |
| JP | 2011-046634 | * 3/2011 ............... A61K 8/60 |
| JP | 201146634 | 3/2011 |
| KR | 10-2004-0033376 A | 4/2004 |
| WO | WO 03002700 A1 | 1/2003 |
| WO | WO 03006146 A1 | 1/2003 |
| WO | WO2004108063 | 12/2004 |
| WO | WO 2006007925 A1 | 1/2006 |
| WO | WO 2006007945 A1 | 1/2006 |
| WO | WO 2010108756 A2 | 9/2010 |
| WO | WO2012167815 A1 | 12/2012 |

OTHER PUBLICATIONS

Kulkarni, S., et al., "Production and Isolation of Biosurfactant-Sophorolipid and its Application in Body Wash Formulation", Asian Jr. of Microbiol. Biotech., Env. Sc., Mar. 2011, pp. 217-221, vol. 13, No. 1.

(Continued)

*Primary Examiner* — Brian P Mruk

(74) *Attorney, Agent, or Firm* — Scully, Scott, Murphy & Presser, P.C.

(57) ABSTRACT

The present invention is directed to compositions comprising water, at least one biosurfactant and at least one fatty acid, which are characterized in that the fraction of the sum of all surfactants in the composition is from 1 to 30% by weight, and that the fraction of fatty acid, based on the sum of fatty acid and surfactants, is from 0.1 to 20% by weight, and to the use thereof as or for producing bath additives, shower gel, shampoos, conditioners, body cleansers or skin cleansers.

17 Claims, No Drawings

(56) References Cited

OTHER PUBLICATIONS

International Search Report dated Jul. 9, 2014 received in a corresponding foreign application.
English Abstract of EP 1700618 A1 dated Sep. 13, 2006.
English Abstract of WO 2009138306 A1 dated Nov. 19, 2009.
"Kosmetische Fäbemittel [Cosmetic colorants]" of the Dyes Commission of the German Research Society, Verlag Chemie, Weinheim, 1984, pp. 81 to 106.
Chinese Office Action dated Jul. 29, 2015 received from Chinese Patent Application No. 201280065263.X, together with an English-language translation.

\* cited by examiner

AQUEOUS HAIR AND SKIN CLEANING COMPOSITIONS COMPRISING BIOTENSIDES

The present invention is directed to compositions, in particular hair and skin cleaning compositions, particularly preferably formulations for the cleaning and care of human or animal body parts, in particular skin and hair for hide or feathers. The compositions according to the invention comprise one or more biosurfactants, one or more fatty acids, and water. The compositions can be e.g. cleaning or care formulations, such as e.g. shampoos, conditioners, shower gels, body cleaning compositions or skin cleaning compositions.

There has for a long time been the need to provide mild cleaning compositions which are especially mild to skin and hair. Such cleaning compositions should not only be mild to skin and hair, but also have further desirable properties, such as e.g. good storage stability and good foaming behaviour. Moreover, there is a greater need for surfactants which are based completely on renewable raw materials and can be sustainably produced by means of mild conditions (e.g. by fermentation).

Numerous mild surfactant systems have already been proposed with which it has been attempted to produce corresponding cleaning compositions. Often, the mild surfactant systems exhibited a lower foaming ability, meaning that a greater addition of surfactant system was necessary, which in turn led to lower mildness of the product.

Suitable surfactant systems leading to mild cleaning compositions with usable foam behaviour that have been proposed are those which comprise sulphosuccinates as surfactants in combination with amphoteric surfactants. Such systems are described inter alia in EP 1771148 and EP 1771538.

A disadvantage of sulphosuccinate systems was their unforeseeable behaviour with regard to viscosity adjustment and storage stability, particularly their tendency towards gel formation. According to EP 1771538, the hydrolysis products of the sulphosuccinates are responsible for the poor storage stability of such cleaning compositions.

The prior art discloses the use of so-called biosurfactants for producing compositions for cleaning skin and/or hair and as household cleaner and textile detergent.

U.S. Pat. No. 7,985,722 describes formulations which have rhamnolipids and the use thereof as cleaning, disinfecting or deodorizing compositions. In the examples these formulations, which have 5% of crude rhamnolipid and water and ethanol as solvent/carrier, are used e.g. as shampoo/cleaning composition for pets. For use on people, a 2% strength solution of crude rhamnolipid in water/ethanol was used. The rhamnolipid was added to a basic shampoo formulation. In a concentration range from 0.01 to 35% of concentrated crude rhamnolipid, reddening of the skin was observed here (Example 4).

U.S. Pat. No. 7,556,654 describes organic cleaners which have biosurfactants, in particular sophorolipids, and one or more enzymes.

EP 0 499 434 describes compositions for washing textiles, dishes and surfaces in the home, comprising one or more glycolipid biosurfactants, in particular sophorolipids, glucose lipids, cellobiose lipids, trehalose lipids and rhamnolipids. Here, the examples describe a particularly good washing/cleaning performance if mixtures of glycolipid biosurfactant, in particular rhamnolipid, are used with non-glycolipid biosurfactant, such as e.g. ethoxylated dodecyl alcohol or di-C8-sulphosuccinate. The non-glycolipid biosurfactant is present in the lamellar phase, and the glycolipid biosurfactant is present in the micellar phase.

EP 1 445 302 describes cleaning compositions which have at least one glycolipid biosurfactant and one non-glycolipid biosurfactant, where at least one non-glycolipid biosurfactant is present in the micellar phase.

EP 1 411 111 describes biodegradable low-foaming detergent compositions which have a mixture of two sophorolipids, as well as detergent auxiliary components, selected from enzyme, oxygen bleach, bleach activator, alkaline formative substance, sequestrant, fluid reforming agent and neutral inorganic salt.

WO 03/006146 discloses aqueous preparations comprising surface-active fermentation products and nonionic surfactants, and the use thereof for producing cosmetic preparations.

An object of the present invention was to provide compositions, in particular hair and skin cleaning compositions, particularly preferably formulations for the cleaning and care of human or animal body parts, in particular skin and hair or hide or feathers, which do not have one or more of the disadvantages of the known formulations. The compositions according to the invention should preferably be biodegradable to the greatest possible extent, readily compatible, i.e. cause in particular only slight, if any, reddening of skin and/or eyes, have a good skin care benefit and/or be based as far as possible entirely on natural raw materials.

Surprisingly, it has been found that compositions, as defined in the claims and described below, achieve one or more of the stated objects.

Unexpectedly, in the handwashing test (HWT) it was found that the additionally present fatty acid (oleic acid) has a positive effect and, contrary to expectations, has no significant effects on foam or thickening properties of the surfactant solution.

The present invention therefore provides compositions comprising water, at least one biosurfactant and at least one fatty acid, which are characterized in that the fraction of the sum of all surfactants in the compositions is from 5 to 20% by weight, and that the fraction of fatty acid, based on the sum of fatty acid and surfactants, is from 0.1 to 20% by weight.

Moreover, the present invention provides the use of the compositions according to the invention as or for producing bath additives, shower gel, shampoos, conditioners, impregnation lotions for moist wet wipes, body cleaning compositions or skin cleaning compositions.

An advantage of the composition according to the invention is that the fraction of surfactants present in it which are based on renewable raw materials is preferably more than 50% by weight, based on the total amount of surfactants.

A further advantage of the composition according to the invention is that sugars or sugars and glycerides and/or fatty acids can be used as raw materials for the biosurfactants.

A further advantage of the composition according to the invention is that it is very mild.

It is also an advantage that many of the compositions according to the invention achieve a surprisingly good performance in a panel test (e.g. emollient properties on the skin) compared to formulations with surfactants which are not a biosurfactant and at the same time often have a negligible effect on viscosity and virtually no effect on the foaming ability of the investigated surfactant mixtures.

The compositions according to the invention, and uses thereof are described below by way of example without any intention of limiting the invention to these exemplary embodiments. Wherever ranges, general formulae or compound classes are given below, then these are intended to include not only the corresponding ranges or groups of compounds that are explicitly mentioned, but also all part ranges and part groups of compounds which can be obtained by removing individual values (ranges) or compounds. Wherever documents are cited within the context of the present description, then their contents, in particular as regards the substantive matter to which reference is made, are deemed as belonging in their entirety to the disclosure content of the present invention. Where average values are stated hereinbelow, then, unless stated otherwise, these are number-averaged average values. Unless stated otherwise, percentages are data in percent by weight. Wherever measurement values are stated hereinbelow, then, unless stated otherwise, these have been determined at a temperature of 25° C. and a pressure of 1013 mbar.

The compositions according to the invention comprising water, at least one biosurfactant and at least one fatty acid, are characterized in that the fraction of the sum of all surfactants in the compositions according to the invention is from 0.1 to 30% by weight, preferably 1 to 25% by weight, preferably 2.5 to 20% by weight and particularly preferably 10 to 20% by weight, and that the fraction of fatty acids, based on the sum of fatty acids and surfactants, is from 0.01 to 20% by weight, preferably 0.1 to 15 and preferably from 1 to 10% by weight.

The fraction of biosurfactants in the compositions according to the invention is preferably from 0.1 to 30% by weight, preferably from 0.5 to 20% by weight and particularly preferably from 0.75 to 10% by weight, based on the total composition.

Within the context of the present invention, biosurfactants are understood as meaning all glycolipids produced by fermentation.

Raw materials for producing the biosurfactants that can be used are carbohydrates, in particular sugars such as e.g. glucose and/or lipophilic carbon sources such as fats, oils, partial glycerides, fatty acids, fatty alcohols, long-chain saturated or unsaturated hydrocarbons. Preferably, in the compositions according to the invention, no biosurfactants are present which are not produced by fermentation of glycolipids, such as e.g. lipoproteins.

Preferably, the composition according to the invention has, as biosurfactants, rhamnolipids, sophorolipids, glucoselipids, celluloselipids and/or trehaloselipids, preferably rhamnolipids and/or sophorolipids. The biosurfactants, in particular glycolipid surfactants, can be produced e.g. as in EP 0 499 434, U.S. Pat. No. 7,985,722, WO 03/006146, JP 60 183032, DE 19648439, DE 19600743, JP 01 304034, CN 1337439, JP 2006 274233, KR 2004033376, JP 2006 083238, JP 2006 070231, WO 03/002700, FR 2740779, DE 2939519, U.S. Pat. No. 7,556,654, FR 2855752, EP 1445302, JP 2008 062179 and JP 2007 181789 or the documents cited therein. Suitable biosurfactants can be acquired e.g. from Soliance, France.

Preferably, the composition according to the invention has, as biosurfactants, rhamnolipids, in particular mono-, di- or polyrhamnolipids and/or sophorolipids. Particularly preferably, the composition according to the invention has one or more of the rhamnolipids and/or sophorolipids described in EP 1 445 302 A with the formulae (I), (II) or (III).

Fatty acids which can be present in the compositions according to the invention are all known aliphatic, branched or unbranched, saturated or unsaturated carboxylic acids or (poly)hydroxycarboxylic acids, or di-, tri- or oligomers thereof. Preferably, the composition according to the invention comprises one or more (hydroxy)fatty acids selected from the group comprising formic acid, acetic acid, propionic acid, butyric acid, valeric acid, hexanoic acid (caproic acid), heptanoic acid (oenanthic acid, enanthic acid), octanoic acid (caprylic acid), pelargonic acid (nonanoic acid), decanoic acid (capric acid), undecanoic acid, dodecanoic acid (lauric acid), tridecanoic acid, tetradecanoic acid (myristic acid), pentadecanoic acid, palmitic acid (hexadecanoic acid), margaric acid (heptadecanoic acid), stearic acid (octadecanoic acid), nonadecanoic acid, arachic acid (eicosanoic acid), behenic acid (docosanoic acid), tetracosanoic acid (lignoceric acid), cerotic acid (hexacosanoic acid), triacontanoic acid (melissic acid), isobutyric acid (2-methylpropanoic acid), 3-methylbutyric acid (isovaleric acid, 3-methylbutanoic acid), tuberculostearic acid (10-methyloctadecanoic acid), acrylic acid (propenoic acid) butenoic acid, [crotonic acid, (2E)-but-2-enoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], sorbic acid [(2E,4E)-hexa-2,4-dienoic acid], linoleic acid [(9Z,12Z)-octadeca-9,12-dienoic acid], linolenic acid [(9Z,12Z,15Z)-octadeca-9,12,15-trienoic acid], elaeostearic acid [(9Z,11E,13E)-octadeca-9,11,13-trienoic acid], arachidonic acid [(5Z,8Z,11Z,14Z)-icosa-5,8,11,14-tetraenoic acid], eicosapentaenoic acid [(5Z,8Z,11Z,14Z,17Z)-icosa-5,8,11,14,17-pentaenoic acid], clupanodonic acid [(4Z,8Z,12Z,15Z,19Z)-docosa-4,8,12,15,19-pentaenoic acid], mandelic acid, lactic acid, hydroxysuccinic acid, citric acid, tartaric acid, β-hydroxydecanoic acid or dimer thereof, other fruit acids, ricinoleic acid, and humic acids. Preferably, the composition according to the invention comprises one or more fatty acids selected from valeric acid, hexanoic acid (caproic acid), heptanoic acid (oenanthic acid, enanthic acid), octanoic acid (caprylic acid), pelargonic acid (nonanoic acid), decanoic acid (capric acid), dodecanoic acid (lauric acid), tetradecanoic acid (myristic acid), palmitic acid (hexadecanoic acid), margaric acid (heptadecanoic acid), stearic acid (octadecanoic acid), arachic acid (eicosanoic acid), behenic acid (docosanoic acid), tetracosanoic acid (lignoceric acid), cerotic acid (hexacosanoic acid), triacontanoic acid (melissic acid), tuberculostearic acid (10-methyloctadecanoic acid), palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], sorbic acid [(2E,4E)-hexa-2,4-dienoic acid], linoleic acid [(9Z,12Z)-octadeca-9,12-dienoic acid], linolenic acid [(9Z,12Z,15Z)-octadeca-9,12,15-trienoic acid], elaeostearic acid [(9Z,11E,13E)-octadeca-9,11,13-trienoic acid], arachidonic acid [(5Z,8Z,11Z,14Z)-icosa-5,8,11,14-tetraenoic acid], eicosapentaenoic acid [(5Z,8Z,11Z,14Z,17Z)-icosa-5,8,11,14,17-pentaenoic acid] and clupanodonic acid [(4Z,8Z,12Z,15Z,19Z)-docosa-4,8,12,15,19-pentaenoic acid]. In the composition according to the invention, fatty acids are particularly preferably present which are based on renewable raw materials, in particular on animal or vegetable fats or oils, in particular dimeric β-hydroxydecanoic acid, oleic acid, palmitic acid, stearic acid and/or linoleic acid. The fraction of fatty acids which are not based on renewable raw materials is, based on the total sum of the fatty acids present, preferably less than 10% by weight, preferably less than 1% by weight and particularly preferably less than 0.1% by weight.

The fatty acids present in the composition according to the invention can in particular be those as are optionally used in the process for producing the biosurfactant and/or are optionally produced as by-product. In the case of using a reaction mixture which is produced during the production of the biosurfactant and which has fatty acid, it is possible to dispense with an additional addition of fatty acid if the fraction of the fatty acid corresponds to the aforementioned limits. Moreover, if fatty acid is produced in suitable amounts (as claimed)

in the reaction mixture during the production of the biosurfactant, it is possible to dispense with complex removal of this fatty acid.

It may be advantageous if the composition according to the invention moreover has at least one surfactant which is not a biosurfactant. The weight ratio of biosurfactants to surfactants which are not a biosurfactant in the composition according to the invention can be >1:1 or ≤1:1. Preferably, the weight ratio of biosurfactants to surfactants which are not a biosurfactant is >1:1 or <1:1, preferably >1:1.

As surfactants which are not biosurfactants, the composition according to the invention can have all known surfactants suitable in particular for cosmetic formulations. Preference is given to using those surfactants as are described e.g. in DE 102005011785, EP 2000124 and WO 2010/108756.

Preferably, the composition according to the invention has, as surfactants which are not biosurfactants, surfactants with an anionic, amphoteric/ampholytic and/or zwitterionic structure. Typical examples of mild, i.e. particularly skin compatible, surfactants are fatty alcohol polyglycol ether sulphates, monoglyceride sulphates, alkyl sulphates, mono- and/or dialkyl sulphosuccinates, fatty acid isethionates, fatty acid sarcosinates, fatty acid taurides, fatty acid glutamates, ethercarboxylic acids, alkyl oligoglucosides, alkyl polyglucosides, fatty acid glucamides, alkylamidobetaines and/or alkylbetaines.

Amphoteric surfactants which can be present are e.g. betaines, amphoacetates or amphopropionates, such as e.g. substances like the N-alkyl-N,N-dimethylammoniumglycinates, for example cocoalkyldimethylammoniumglycinate, N-acylaminopropyl-N,N-dimethylammonium glycinates, for example cocoacylaminopropyldimethylammonium glycinate, and 2-alkyl-3-carboxylmethyl-3-hydroxyethylimidazolines each having 8 to 18 carbon atoms in the alkyl or acyl group, as well as cocoacylaminoethylhydroxyethyl carboxymethylglycinate.

Ampholytic surfactants which can be present are those surface-active compounds which, apart from a $C_{8/18}$-alkyl or -acyl group in the molecule, contain at least one free amino group and at least one COOH or $SO_3H$ group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each having about 8 to 18 carbon atoms in the alkyl group. Further examples of ampholytic surfactants are N-cocoalkylaminopropionate, cocoacylaminoethylaminopropionate and $C_{12/18}$-acylsarcosine.

Preferred anionic surfactants are e.g. the salts of various cations (sodium, ammonium or others) of cocoylglutamates, lauryl glucose carboxylate etc. Zwitterionic surfactants which can be present in the formulation are e.g. cocamidopropylbetaine or cocoamidopropylsultaine. Preferred amphoteric surfactants are, in particular, amphoacetates such as sodium cocoamphoacetate or disodium cocoamphodiacetate.

Preference is given to compositions which comprise at least one surfactant from the group comprising lauryl ether sulphates, alkyl sulphates, alkyl oligoglucosides, mono- and/or dialkyl sulphosuccinates, alkylamidobetaines or fatty acid sarcosinates as non-biosurfactant.

Particularly preferred compositions comprise no surfactants which have sulphates or polyethylene glycol.

The compositions according to the invention can have dyes. Dyes that can be used are e.g. the substances approved and suitable for cosmetic purposes, as are listed for example in the publication "Kosmetische Farbemittel [Cosmetic colorants]" of the Dyes Commission of the German Research Society, Verlag Chemie, Weinheim, 1984, pages 81 to 106.

It may be advantageous if the compositions according to the invention have one or more natural dyes. Within the context of the present invention, natural dyes are understood as meaning mineral dyes or dyes obtained from plants or animals. All natural dyes can be used in the compositions according to the invention. Preferred naturally occurring dyes are, e.g. indigo, lawson, purple, carmine, kermes, alizarin, woad, crocetin, brasilin, saffron, crocetin, curcumia, curcumin, orlean, bixin, annatto, anthocyans, betanin, capsanthin, carotene, chlorophylls, carminic acid, lutein, xanthophyll, lycopene, vegetable black or caramel. Particular preference is given to using natural dyes which are obtained from plants or animals.

Particularly preferably used natural substances are bixin (E 160b), anthocyans (E 163), betanin (E 162), capsanthin (E 160c), carotene (E 160a), chlorophylls (E 140), curcumin (E 100), carminic acid (E 120), luteine (E 161b), xanthophyll, lycopene (E 160d), vegetable black (E 153) and/or caramel (E 150a).

The composition according to the invention particularly preferably has exclusively natural dyes as dyes.

The fraction of dyes, preferably natural dyes, in the compositions according to the invention is preferably from 0.001 to 1% by weight.

The use of natural dyes achieves better biodegradability and tolerability (mildness) of the composition according to the invention.

The composition according to the invention can have preservatives, e.g. those as are listed in the EC regulation (Regulation (EC) No. 1223/2009 of the European Parliament and of the Council of 30 Nov. 2009 on cosmetic products, Annex V). Preferred compositions according to the invention are those which comprise, as preservatives, one or a combination of the following substances: benzyl alcohol, sodium benzoate, potassium sorbate, DMDM hydantoin, formic acid, benzoic acid or polyaminopropyl biguanide. Particularly preferred compositions, however, are those which are free from preservatives, in particular free from those according to the EU Regulation.

It may be advantageous if the composition according to the invention comprises propylene glycol, urea, glycerol, essential oils, phenylethyl alcohol and/or ethanol. Preferably, the fraction of the sum of propylene glycol, urea, glycerol, essential oils, phenylethyl alcohol and ethanol in the composition is from 0.01 to 15% by weight, preferably from 0.1 to 10% by weight. By using one or more of the specified substances it is possible to prevent or at least reduce an increase in the germ count.

It may be advantageous if the composition according to the invention comprises at least one thickener. The fraction of thickeners in the composition is preferably from 0.05 to 20% by weight, preferably from 0.1 to 10% by weight and particularly preferably from 0.5 to 5% by weight, based on the composition.

As thickener, the composition according to the invention preferably has one or more thickeners, such as e.g. relatively high molecular weight ones, preferably PEG>10, preferably >100, polyethylene glycol mono- and diesters of fatty acids, such as e.g. PEG 18 glyceryl oleate, PEG 55 polypropylene glycol oleate, PEG 120 methyl glucose dioleate or PEG 200 hydrogenated glyceryl palmate, preferably PEG free thickeners, preferably selected from polysaccharides, in particular xanthan gum, guar and guar derivatives, agar agar, alginates, and tyloses, cellulose or cellulose derivatives, such as e.g. ethylcellulose, carboxymethylcellulose, hydroxyethylcellulose or hydroxymethlypropylcellulose, alkyl-modified sugar derivatives, such as e.g. cetylhydroxyethylcellulose, carbomers (crosslinked polyacrylates), polyacrylamides, polyvinyl alcohol and polyvinylpyrrolidone, ethoxylated fatty acid glycerides, esters of fatty acids with polyols, such as for example pentaerythritol or trimethylolpropane, fatty alcohol ethoxylates and alkyl oligoglucosides.

Preferred compositions according to the invention are those which have a combination of a polymeric thickener for the water phase and a polymeric thickener for the oil phase.

Particularly preferred compositions are those in which exclusively thickeners (i.e. at least 90% by weight, preferably 100% by weight, of the thickeners present) are present which are based in part or completely, in particular completely, on renewable raw materials, such as e.g. xanthan gum, guar and guar derivatives, agar agar, alginates, and tyloses, cellulose or cellulose derivatives.

It can be advantageous if the composition according to the invention has perfume oils or fragrances. Perfumes oils that can be used are all known perfume oils and in particular the perfume oils suitable for producing cosmetic formulations. Suitable perfume oils can be found e.g. in the product catalogues of known manufacturers, such as, for example, Symrise, Frey&Lau or IFF. Preferably, the composition according to the invention has perfume oils or fragrances, where the fraction of natural fragrances, based on the total number of fragrances in the perfume oils, is at least 50% by weight, preferably at least 75% and preferably at least 95% by weight.

Natural fragrances which can be used are, e.g. extracts from flowers (lily, lavender, rose, jasmine, neroli, ylang ylang), stems and leaves (geranium, patchouli, petitgrain), fruits (anise, coriander, caraway, juniper), fruit peels (bergamot, lemon, orange), roots (mace, angelica, celery, cardamom, costus, iris, thyme), needles and branches (spruce, fir, pine, dwarf-pine), resins and balsams (galbanum, elemi, benzoin, myrrh, olibanum, opoponax). Animal raw materials are also suitable as natural fragrances, such as, for example, civet and castoreum. Essential oils are also suitable as perfume oils, such as, for example, sage oil, camomile oil, clove oil, melissa oil, mint oil, cinnamon leaf oil, linden blossom oil, juniper berry oil, vetiver oil, olibanum oil, galbanum oil, labdanum oil, lavandin oil, bergamot oil, lemon oil, mandarin oil, orange oil, clary sage oil or geranium oil.

The compositions according to the invention can comprise, as further components, in particular e.g. those which are e.g. selected from the group of emollients, emulsifiers, viscosity regulators/stabilizers, UV photoprotective filters, antioxidants, solids and fillers, film formers, pearlescent additives, deodorant and antiperspirant active ingredients, insect repellents, self-tanning agents, conditioners, (cosmetic) active ingredients, care additives, superfatting agents, solubility promoters (solubilizers), pearlizing agents and solvents, with the proviso that the specified components are not identical to the biosurfactants, surfactants, thickeners. Substances which can be used as exemplary representatives of the individual groups are known to the person skilled in the art and can be found for example in the applications DE 102008001788 A1, DE 102005011785 A1 and EP 2000124A. The substances specified therein as being preferred should also be deemed to be preferred substances within the context of the present invention. The patent applications are hereby incorporated by reference and thus form part of the disclosure. Preferred compositions according to the invention have in particular solubility promoters (solubilizers) for water-insoluble substances and active ingredients for caring for skin and hair, such as e.g. refatting agents. The fraction of the sum of the other components specified in this section in the composition according to the invention is preferably from 3 to 50% by weight, preferably from 5 to 25% by weight.

Within the context of the present invention, solubilizer or solubility promoter is the term used to refer to a substance which is able to bring water-insoluble compounds into solution as clearly as possible in aqueous systems. According to generally accepted postulation, in this process, aggregates such as micelles are formed in whose structures the hydrophobic substances are integrated. The formation of a "microemulsion", i.e. of a thermodynamically stable mixture of water (aqueous solution), an oil (substance immiscible with water) and a solubilizer or solubility promoter is optimal. Typical solubilizers are ethoxylated fatty derivatives and polyglycerol fatty acid esters.

Care active ingredients or emollients that can be used are in particular e.g. isopropyl myristate, sucrose cocoate, ethoxylated glycerol fatty acid esters, such as, for example, PEG 7 glyceryl cocoate (such as e.g. TEGOSOFT® GC available from Evonik Industries AG), polyglycerol fatty acid esters such as polyglyceryl 3 caprate or cationic polymers, such as, for example, polyquaternium 7. These are also referred to as refatting agents.

Particularly preferred compositions according to the invention are free from polyethylene glycol (PEG) and/or derivatives thereof and are preferably also free from propylene glycol (PPG) and/or derivatives thereof.

Further particularly preferred compositions according to the invention are free from sulphates and moreover free from polyethylene glycol (PEG) and/or derivatives thereof and propylene glycol (PPG) and/or derivatives thereof.

The compositions according to the invention preferably have a pH, determined by means of a pH meter of the PB 11 type from Sartorius, from 5 to 8.

Preferred compositions have a viscosity, determined at 25° C. using a DV-I Prime Brookfield viscometer type from 500 to 20 000 mPas.

The compositions according to the invention are preferably a body, skin or hair treatment composition for treating people and/or animals, in particular people and mammals.

A composition according to the invention can be in particular a shampoo, a conditioner, a shower gel, a body cleaning composition or a skin cleaning composition. Compositions according to the invention are preferably liquid, cosmetic, dermatological or pharmaceutical body cleaning compositions, in particular shower baths and gels, bath formulations, liquid soaps and shampoos, or are used for producing these products/formulations.

The compositions according to the invention can be in particular a bath additive, shampoo, conditioner, shower gel, body cleanser, impregnation solutions for wet cleansing wipes or skin cleansers or be used for producing one or more of these products.

Particularly preferred compositions are those which combine some or all of the aforementioned preferred features.

The present invention is described by way of example in the examples listed below without any intention of limiting the invention, the scope of application of which arises from the entire description and the claims, to the embodiments specified in the examples.

EXAMPLES

Unless stated otherwise, all concentrations in the application examples are given in percent by weight. Customary formulation methods known to the person skilled in the art were used to prepare the compositions.

Product Example 1

Sophorolipid

The sophorolipid was prepared by means of fermentation with the yeast *Candida bombicola* based on the substrates glucose, sunflower oil, rapeseed oil or olive oil (comprising predominantly oleic acid as fatty acid fraction).

The growth medium comprised the following constituents:
10.0 g/L glucose ((D)+-glucose·1H$_2$O)
7.5 g/L YNB (Yeast Nitrogen Base)
2.0 g/L yeast extract 1.1 L of the medium were autoclaved in a fermenter with an operating volume of 2 L and inoculated with a preculture, which was in the exponential phase, from the same medium. The temperature was adjusted to 30° C. The pO2 was maintained via the stirrer speed at 30% relative saturation upon gassing with air; the stirrer speed, however, was never less than 200 rpm. During the biomass formation phase, the pH dropped to 3.5 and was held at this value by adding NaOH. After the biomass formation phase was complete (consumption of the glucose present, characterized by the increase in pO$_2$, or decrease in pCO$_2$), the product formation phase was initiated by adding 150 g of the corresponding oil, 200 mL of a 750 g/L glucose solution and 10 mL of a 150 g/L yeast extract solution. The end of the product formation phase was characterized by the renewed increase in pO2. After the fermentation was complete, the mixture was autoclaved, during which the crude product phase settled out. The crude product phase was washed with water. The product phase was then extracted with ethyl acetate and then the solvent was removed in vacuo. Analysis by means of HPLC-MS and NMR revealed that the product comprised, besides the sophorolipid, also about 10% by weight of unreacted free fatty acid (in particular oleic acid), based on sophorolipids. The residual fatty acid was removed from the product by means of multiple extraction with n-hexane at pH 3 so that the residual amount of free fatty acid was <0.1% by weight (HPLC). A colourless solid was obtained.

Product Example 1b

Sophorolipid+10% Oleic Acid

Product example 1a was admixed with 10% by weight of technical-grade oleic acid (Cremer Oleo GmbH and Co. KG, Germany).

Product Example 2a

Rhamnolipid

Product obtainable from Rhamnolipids, Inc., USA, as 25% strength aqueous solution. HPLC analysis ensures that no free fatty acids (i.e. <0.1% by weight, based on the total composition of the product) are contained as secondary constituent.

Product Example 2b

Rhamnolipid+10% Oleic Acid

Product example 2a was admixed with 10% by weight of technical-grade oleic acid with respect to the rhamnolipid.

Skin Compatibility According to RBC Test:

In the so-called RBC test (Red Blood Cell-Test, see W. J. W. Pape, U. Pfannenbecker, U. Hoppe, Mol. Toxicol. 1987, 1, 525), the products 1a, 1b, 2a and 2b exhibit very good skin compatibility. The L/D values are >100. Accordingly, the products are classed as non-irritative in this test.

Applications-Related Testing:

Testing the Skin Care Benefit and Foam Properties by Means of a Handwashing Test To evaluate the skin care benefit and the foam properties of product examples 1a, 1b, 2a and 2b according to the invention in aqueous, surface-active compositions (surfactant formulations), sensor handwashing tests were carried out compared to the secondary surfactant cocamidopropyl betaine. Cocamidopropyl betaine is very widespread in the industry as a universally applicable, mild and foam-promoting secondary surfactant and is a highly effective component in aqueous, surface-active formulations.

A group consisting of 10 trained test persons washed their hands in a defined manner in this handwashing test and assessed foam properties and skin feel using a grading scale from 1 (poor) to 5 (very good). The products used were in each case tested in a standardized surfactant formulation (Table 1).

A surfactant formulation without the addition of a secondary surfactant was used as control formulation 3. The surfactant formulations 6, 8 and 9 are the compositions according to the invention and the surfactant formulations 4, 5 and 7 are the composition not according to the invention (Table 1).

TABLE 1

Test formulations for handwashing test according to (data in % by weight).

| Formulation examples | 3 | 4 | 5 | 6 | 7 | 8 | 9 |
|---|---|---|---|---|---|---|---|
| Texapon ® NSO (BASF Cognis, INCI: Sodium Laureth Sulfate, 28% strength) | 32.1 | 32.1 | 32.1 | 32.1 | 32.1 | 32.1 | 32.1 |
| TEGO ® Betain F 50 (Evonik Industries AG, INCI: Cocamidopropyl Betaine, 38% strength) | | 7.9 | | | | | |
| Product example 1a: Sophorolipid (100% strength) | | | 3.0 | | | | |
| Product example 1b: 90% Sophorolipid + 10% oleic acid | | | | 3.0 | | | 1.5 |
| Product example 2a: Rhamnolipid (25% strength aqueous solution) | | | | | 12.0 | | |
| Product example 2b: 90% Rhamnolipid + 10% oleic acid (25% strength aqueous solution) | | | | | | 12.0 | 6.0 |
| NaCl | 4.5 | 4.5 | 4.5 | 4.5 | 4.5 | 4.5 | 4.5 |
| Citric Acid, 30% | ad pH 6.0 | | | | | | |
| Water, demineralized | ad 100% | | | | | | |

Table 2 shows the results of the handwashing test.

TABLE 2

Results of the handwashing test

| Test formulation | 3 | 4 | 5 | 6 | 7 | 8 | 9 |
|---|---|---|---|---|---|---|---|
| Foaming behaviour | 2.2 | 3.1 | 3.0 | 3.0 | 3.4 | 3.3 | 3.3 |
| Foam creaminess | 2.0 | 2.8 | 2.4 | 2.3 | 3.0 | 3.0 | 2.9 |
| Skin feel during washing | 2.9 | 3.3 | 3.4 | 3.6 | 3.4 | 3.5 | 3.5 |
| Ease of rinsing | 4.0 | 4.1 | 4.4 | 4.5 | 4.0 | 4.2 | 4.4 |
| Skin smoothness after 3 min | 2.8 | 3.1 | 3.0 | 3.2 | 3.3 | 3.6 | 3.5 |
| Skin softness after 3 min | 3.0 | 3.1 | 3.0 | 3.2 | 3.4 | 3.5 | 3.4 |

It is evident from the measurement results in Table 2 that the composition 6 according to the invention using product example 1b (sophorolipid+10% oleic acid) has a better skin feel during washing with the formulation and surprisingly easier rinseability compared to the comparison composition 4 according to the prior art. The easy rinseability is an ever more important parameter in the development of new environmentally friendly cosmetic products since water savings during washing lead to significantly better ecobalances. Moreover, it is evident that the composition 6 according to the invention was assessed better for skin feel, skin smoothness and skin softness than test formulation 5 without oleic acid. Surprisingly, however, the foam properties are barely influenced here.

The control formulation 3 has the poorest values in all properties. Furthermore, it is evident from the measurement values that the composition 8 according to the invention with product example 2b (rhamnolipid+10% oleic acid) and also the formulation 9 with both product examples (1b and 2b, 50:50) surprisingly brings about a clear improvement in the foam properties and the skin feel during washing and after application and drying compared to the prior art (formulation 4). Compared to formulation 7 (rhamnolipid without oleic acid), formulations 8 and 9 exhibited advantages specifically in the case of skin smoothness and in the case of rinseability.

Contrary to expectations, in the present formulations, a certain fraction of free fatty acid in the biosurfactant exhibited no adverse effect on the foaming behaviour or the thickening properties.

Further Formulation Examples

The formulation examples given in the tables below show exemplary representatives of a large number of possible compositions according to the invention.

The raw materials used are listed with the INCI name.

Unless stated otherwise, the data in the tables are data in % by weight. The use concentrations are given in % by weight of active substance.

If the preparation of the formulation requires the separate preparation or mixing of formulation constituents beforehand, this is termed multiphase preparation. If a two-phase preparation is required, the two phases are labelled A and B in the stated tables. In the case of three- or four-phase processes, the phases are called A, B, C and D.

Lauryl Ether Sulphate-Based Systems:

TABLE 3

Conditioning antidandruff shampoo

| | | |
|---|---|---|
| A | Glycol Distearate | 3.0% |
| | Sodium Laureth Sulfate | 8.0% |
| B | Perfume | q.s. |
| | Zinc Pyrithione | 1.0% |
| | Silicone Quaternium-22 | 1.0% |
| C | Water | ad 100% |
| | Acrylates/C10-30 Alkyl Acrylate Crosspolymer | 0.2% |
| | Polyquaternium-10 | 0.3% |
| | NaOH, 25% | 0.3% |
| D | Undecylenamidopropyl Betaine | 2.5% |
| | Product example 1b: Sophorolipid + 10% oleic acid | 2.5% |
| | Preservative | q.s |

TABLE 4

Conditioning antidandruff shampoo

| | | |
|---|---|---|
| A | Glycol Distearate | 3.0% |
| | Sodium Laureth Sulfate | 10.0% |
| B | Perfume | q.s. |
| | Zinc Pyrithione | 1.0% |
| | Quaternium-80 | 0.5% |
| C | Water | ad 100% |
| | Carbomer | 0.5% |
| | Polyquaternium-10 | 0.3% |
| | NaOH, 25% | 0.8% |

TABLE 4-continued

Conditioning antidandruff shampoo

| | | |
|---|---|---|
| D | Undecylenamidopropyl Betaine | 3.0% |
| | Product example 2b: Rhamnolipid + 10% oleic acid | 2.0% |
| | Preservative | q.s. |

TABLE 5

Conditioning antidandruff shampoo

| | | |
|---|---|---|
| A | Glycol Distearate | 3.0% |
| | Sodium Laureth Sulfate | 9.0% |
| B | Perfume | q.s |
| | Climbazole | 0.1% |
| | Quaternium-80 | 1.0% |
| C | Water | ad 100% |
| | Acrylates/C10-30 Alkyl Acrylate Crosspolymer | 0.3% |
| | Polyquaternium-10 | 0.2% |
| | NaOH, 25% strength | 0.3% |
| D | Undecylenamidopropyl Betaine | 3.5% |
| | Product example 1b: Sophorolipid + 10% oleic acid | 1.5% |
| | Preservative | q.s |

TABLE 6

Conditioning antidandruff shampoo

| | | |
|---|---|---|
| A | PEG-3 Distearate | 2.5% |
| | Sodium Laureth Sulfate | 10.0% |
| B | Perfume | q.s. |
| | Octopirox | 0.3% |
| | Dimethicone | 0.5% |
| C | Water | ad 100% |
| | Acrylates/C10-30 Alkyl Acrylate Crosspolymer | 0.2% |
| | Polyquaternium-10 | 0.3% |
| | NaOH, 25% | 0.3% |
| D | Undecylenamidopropyl Betaine | 2.0% |
| | Product example 2b: Rhamnolipid + 10% oleic acid | 3.0% |
| | Preservative, Dyes | q.s |

TABLE 7

Moisturizing skin cleanser

| | | |
|---|---|---|
| A | Sodium Laureth Sulfate | 8.0% |
| | Product example 1b: Sophorolipid + 10% oleic acid | 1.0% |
| | Perfume | q.s. |
| B | Water | ad 100% |
| | Hydroxypropyl Methylcellulose | 1.2% |
| | Cocamidopropyl Betaine | 3.0% |
| | PPG-3 Myristyl Ether | 1.0% |
| | Glycol Distearate | 2.0% |
| | PEG-200 Hydrogenated Glyceryl Palmate (and) PEG-7 Glyceryl Cocoate | 1.0% |
| | Preservative | q.s. |
| | Citric Acid, 30% | ad pH 5.5 |

TABLE 8

Moisturizing skin cleanser

| | | |
|---|---|---|
| A | Sodium Laureth Sulfate | 7.0% |
| | Product example 2b: Rhamnolipid + 10% oleic acid | 3.0% |
| | Perfume | q.s. |
| B | Water | ad 100% |
| | Hydroxypropyl Methylcellulose | 1.2% |
| | Cocamidopropyl Betaine | 2.0% |
| | PPG-3 Myristyl Ether | 1.0% |
| | PEG-3 Distearate | 1.0% |

TABLE 8-continued

Moisturizing skin cleanser

| | |
|---|---|
| PEG-200 Hydrogenated Glyceryl Palmate (and) PEG-7 Glyceryl Cocoate | 1.0% |
| Preservative | q.s. |
| Citric Acid, 30% | ad pH 5.7 |

TABLE 9

Body cleanser

| | | |
|---|---|---|
| A | Sodium Laureth Sulfate | 8.5% |
| | Product example 2b: Rhamnolipid + 10% oleic acid | 1.5% |
| | Bis-PEG/PPG-20/20 Dimethicone | 0.3% |
| | Perfume | q.s. |
| B | Water | ad 100% |
| | Hydroxypropyl Methylcellulose | 1.2% |
| | Sodium Cocoamphoacetate | 2.5% |
| | PEG-3 Distearate | 2.0% |
| | PEG-200 Hydrogenated Glyceryl Palmate (and) PEG-7 Glyceryl Cocoate | 1.6% |
| | Preservative | q.s. |
| | Citric Acid, 30% | ad pH 5.8 |

TABLE 10

Body cleanser

| | | |
|---|---|---|
| A | Sodium Laureth Sulfate | 8.0% |
| | Product example 1b: Sophorolipid + 10% oleic acid | 1.2% |
| | Bis-PEG/PPG-20/20 Dimethicone | 0.3% |
| | Perfume | q.s. |
| B | Water | ad 100% |
| | Hydroxypropyl Methylcellulose | 1.2% |
| | Citric Acid Monohydrate | 0.5% |
| | Sodium Cocoamphoacetate | 3.0% |
| | Glycol Distearate (and) Laureth-4 (and) Cocamidopropyl Betaine | 2.0% |
| | PEG-200 Hydrogenated Glyceryl Palmate (and) PEG-7 Glyceryl Cocoate | 1.6% |
| | Preservative | q.s. |
| | Citric Acid, 30% | ad pH 5.5 |

TABLE 11

Body cleansing foam

| | |
|---|---|
| Sodium Laureth Sulfate | 3.5% |
| Product example 2b: Rhamnolipid + 10% oleic acid | 3.0% |
| Sodium Cocoamphoacetate | 3.0% |
| Water | ad 100% |
| Hydroxypropyl Methylcellulose | 0.5% |
| Sodium Lactate (and) Sodium PCA (and) Glycine (and) Fructose (and) Urea (and) Niacinamide (and) Inositol (and) Sodium Benzoate (and) Lactic Acid | 1.0% |
| Citric Acid | ad pH 5.5 |
| Perfume | q.s. |

TABLE 12

Body cleansing foam

| | |
|---|---|
| Sodium Laureth Sulfate | 3.5% |
| Product example 1b: Sophorolipid + 10% oleic acid | 3.6% |
| Product example 2b: Rhamnolipid + 10% oleic acid | 0.7% |
| Sodium Cocoamphoacetate | 2.0% |
| Water | ad 100% |
| Hydroxypropyl Methylcellulose | 0.5% |
| Sodium Lactate (and) Sodium PCA (and) Glycine (and) Fructose (and) Urea (and) Niacinamide (and) Inositol (and) Sodium Benzoate (and) Lactic Acid | 0.5% |

TABLE 12-continued

Body cleansing foam

| | |
|---|---|
| Panthenol | 0.2% |
| Citric Acid Monohydrate | ad pH 4.9 |
| Perfume | q.s. |

TABLE 13

Clear conditioning shampoo

| | |
|---|---|
| Sodium Laureth Sulfate | 9.0% |
| Palmitamidopropyltrimonium Chloride | 1.0% |
| PEG-200 Hydrogenated Glyceryl Palmate (and) PEG-7 Glyceryl Cocoate | 2.0% |
| Product example 2b: Rhamnolipid + 10% oleic acid | 0.7% |
| Water | ad 100% |
| Creatine | 1.0% |
| Hydroxypropyl Guar Hydroxypropyltrimonium Chloride | 0.2% |
| Cocamidopropyl Betaine | 2.0% |
| NaCl | 0.5% |
| Perfume | q.s. |
| Preservative | q.s. |

TABLE 14

Clear conditioning shampoo

| | |
|---|---|
| Sodium Laureth Sulfate | 8.0% |
| PEG-200 Hydrogenated Glyceryl Palmate (and) PEG-7 Glyceryl Cocoate | 2.0% |
| Product example 1b: Sophorolipid + 10% oleic acid | 1.5% |
| Water | ad 100% |
| Polyquaternium-10 | 0.2% |
| Cocamidopropyl Betaine | 3.0% |
| NaCl | 0.3% |
| Perfume | q.s. |
| Preservative | q.s. |

TABLE 15

Cloudy conditioning shampoo

| | |
|---|---|
| Sodium Laureth Sulfate | 8.0% |
| PEG-200 Hydrogenated Glyceryl Palmate (and) PEG-7 Glyceryl Cocoate) | 2.0% |
| Product example 1b: Sophorolipid + 10% oleic acid | 1.5% |
| Product example 2b: Rhamnolipid + 10% oleic acid | 0.7% |
| Water | ad 100% |
| Polyquaternium-10 | 0.2% |
| Cocamidopropyl Betaine | 1.5% |
| Dimethicone (and) Dimethiconol | 1.0% |
| Glycol Distearate (and) Laureth-4 (and) Cocamidopropyl Betaine | 2.0% |
| NaCl | 0.3% |
| Perfume | q.s. |
| Preservative | q.s. |

TABLE 16

Body cleanser with pearl effect

| | |
|---|---|
| Sodium Laureth Sulfate | 9.0% |
| Product example 1b: Sophorolipid + 10% oleic acid | 2.5% |
| Water | ad 100% |
| Cocamidopropyl Betaine | 1.5% |
| Glycol Distearate (and) Laureth-4 (and) Cocamidopropyl Betaine | 2.0% |
| PEG-18 Glyceryl Oleate/Cocoate | 1.5% |
| NaCl | 0.5% |

TABLE 16-continued

Body cleanser with pearl effect

| | |
|---|---|
| Perfume | q.s. |
| Preservative | q.s. |

TABLE 17

Shower gel

| | |
|---|---|
| Sodium Laureth Sulfate | 4.0% |
| Product example 2b: Rhamnolipid + 10% oleic acid | 2.5% |
| Sodium Cocoyl Hydrolyzed Wheat Protein Glutamate | 1.5% |
| Disodium PEG-5 Laurylcitrate Sulfosuccinate (and) Capryl/Capramidopropyl Betaine | 2.5% |
| Water | ad 100% |
| Cocamidopropyl Betaine | 3.0% |
| Capryl/Capramidopropyl Betaine | 1.0% |
| Polyquaternium-7 | 0.5% |
| PEG-200 Hydrogenated Glyceryl Palmate (and) PEG-7 Glyceryl Cocoate | 1.8% |
| Perfume | q.s. |
| Preservative | q.s. |

TABLE 18

Shower gel

| | |
|---|---|
| Water | ad 100% |
| Sodium Laureth Sulfate | 5.0% |
| Product example 1b: Sophorolipid + 10% oleic acid | 2.5% |
| Sodium Cocoyl Hydrolyzed Wheat Protein Glutamate | 1.5% |
| Disodium PEG-5 Laurylcitrate Sulfosuccinate (and) Capryl/Capramidopropyl Betaine | 2.5% |
| Cocamidopropyl Betaine | 3.0% |
| Capryl/Capramidopropyl Betaine | 2.0% |
| PEG-200 Hydrogenated Glyceryl Palmate (and) PEG-7 Glyceryl Cocoate | 1.8% |
| Preservative, perfume, dyes | q.s. |

TABLE 19

Shower gel

| | |
|---|---|
| Water | ad 100% |
| Sodium Laureth Sulfate | 9.0% |
| Product example 1b: Sophorolipid + 10% oleic acid | 4.0% |
| Sodium Cocoamphoacetate | 1.5% |
| Capryl/Capramidopropyl Betaine | 1.5% |
| PEG-200 Hydrogenated Glyceryl Palmate (and) PEG-7 Glyceryl Cocoate | 0.5% |
| Citric Acid, 30% | ad pH 6.1 |
| Preservative, perfume | q.s. |

TABLE 20

Clear shower gel

| | |
|---|---|
| Water | ad 100% |
| Sodium Laureth Sulfate | 11.0% |
| Product example 2b: Rhamnolipid + 10% oleic acid | 2.0% |
| PEG-40 Hydrogenated Castor Oil | 2.5% |
| Cocamidopropyl Betaine | 2.0% |
| Sodium Lactate (and) Sodium PCA (and) Glycine (and) Fructose (and) Urea (and) Niacinamide (and) Inositol (and) Sodiumbenzoate (and) Lactic Acid | 1.0% |
| PEG-18 Glyceryl Oleate/Cocoate | 2.0% |
| Preservative, perfume | q.s. |

TABLE 21

Hair and body cleanser

| | |
|---|---|
| Sodium Laureth Sulfate | 7.0% |
| Coco-Betaine | 3.0% |
| Product example 1b: Sophorolipid + 10% oleic acid | 1.5% |
| Product example 2b: Rhamnolipid + 10% oleic acid | 1.5% |
| Polyquaternium-10 | 0.2% |
| PEG-150 Distearate | 1.5% |
| Hydrogenated Didecene | 1.5% |
| Water | ad 100% |
| Citric Acid | ad pH 6.0 |
| Preservative, perfume, dyes | q.s. |

TABLE 22

Washing lotion for sensitive skin

| | |
|---|---|
| Water | ad 100% |
| Sodium Laureth Sulfate | 7.5% |
| Cocamidopropyl Betaine | 3.0% |
| Glyceryl Oleate | 3.0% |
| Product example 1b: Sophorolipid + 10% oleic acid | 2.0% |
| Sodium Chloride | 2.0% |
| Glycol Distearate | 1.0% |
| Sodium Lactate | 1.0% |
| Disodium Cocoyl Glutamate | 1.0% |
| Starch Hydroxypropyltrimonium Chloride | 0.5% |
| Glyceryl Stearate | 0.4% |
| Allantoin | 0.1% |
| Isopropyl Alcohol | 0.1% |
| Alcohol | 0.1% |
| Sorbitol | 0.1% |
| Urea | 0.2% |
| Serine | 0.05% |
| Tocopherol | 0.05% |
| Citric Acid | ad pH 5.5 |
| Preservative, perfume | q.s. |

TABLE 23

Antidandruff shampoo

| | |
|---|---|
| Water | ad 100% |
| Sodium Laureth Sulfate | 7.0% |
| Sodium Lauryl Sulfate | 4.0% |
| Product example 1b: Sophorolipid + 10% oleic acid | 3.0% |
| Cocamide MEA | 2.5% |
| Zinc Carbonate | 1.0% |
| Glycol Distearate | 1.0% |
| Sodium Chloride | 1.0% |
| Zinc Pyrithione | 1.0% |
| Dimethicone | 1.0% |
| Cetyl Alcohol | 0.5% |
| Polyquaternium-10 | 0.2% |
| Sodium Xylenesulfonate | 0.2% |
| Ammonium Laureth Sulfate | 0.2% |
| Sodium Diethylenetriamine-Pentamethylene Phosphonate | 0.1% |
| Etidronic Acid | 0.1% |
| DMDM Hydantoin | 0.1% |
| Disodium EDTA | 0.1% |
| Tetrasodium EDTA | 0.05% |
| Preservative, perfume, dyes | q.s. |

TABLE 24

Shampoo

| | |
|---|---|
| Water | ad 100% |
| Sodium Laureth Sulfate | 5.0% |
| Product example 2b: Rhamnolipid + 10% oleic acid | 4.0% |
| Cocamidopropyl Betaine | 2.0% |
| Sodium Chloride | 2.0% |
| PEG-3 Distearate | 1.5% |

TABLE 24-continued

Shampoo

| | |
|---|---|
| Polyquaternium-10 | 0.3% |
| *Citrus Aurantifolia* Fruit Juice | 0.2% |
| *Paulinia Cupana* Extract | 0.2% |
| PEG-40 Hydrogenated Castor Oil | 0.2% |
| Propylene Glycol | 0.2% |
| Glycerin | 0.2% |
| Citric Acid | ad pH 5.0 |
| Preservative, perfume | q.s. |

TABLE 25

Shampoo

| | |
|---|---|
| Water | ad 100% |
| Sodium Laureth Sulfate | 7.0% |
| Cocamidopropyl Betaine | 2.5% |
| Product example 1b: Sophorolipid + 10% oleic acid | 1.5% |
| Sodium Chloride | 1.5% |
| Glycol Distearate | 1.0% |
| Hydroxypropyl Guar Hydroxypropyltrimonium Chloride | 0.3% |
| Propylene Glycol | 0.3% |
| Panthenol | 0.3% |
| Dimethicone Propyl PG-Betaine | 0.3% |
| Glyoxylic Acid | 0.02% |
| Coumarin | 0.01% |
| Citric Acid | ad pH 5.5 |
| Preservative, perfume | q.s. |

TABLE 26

Shampoo

| | |
|---|---|
| Water | ad 100% |
| Sodium Laureth Sulfate | 5.0% |
| TEA-cocoyl Glutamate | 3.0% |
| Glycerin | 3.0% |
| Product example 2b: Rhamnolipid + 10% oleic acid | 2.0% |
| Sodium Chloride | 2.0% |
| Coco-Betaine | 1.0% |
| Cocamide MIPA | 0.5% |
| Glycol Distearate | 0.5% |
| Sodium Methyl Cocoyl Taurate | 0.4% |
| Sodium PCA | 0.2% |
| Hexylene Glycol | 0.1% |
| Polyquaternium-10 | 0.1% |
| Disodium Cocoamphodiacetate | 0.2% |
| Ceteareth-60 Myristyl Glycol | 0.2% |
| *Brassica Campestris* Seed Oil (Seed) | 0.1% |
| Citric Acid | ad pH 5.5 |
| Preservative, perfume | q.s. |

TABLE 27

Shampoo

| | |
|---|---|
| Water | ad 100% |
| Sodium Laureth Sulfate | 5.0% |
| Product example 1b: Sophorolipid + 10% oleic acid | 3.5% |
| Sodium Laureth-4 Carboxylate | 1.5% |
| Dipropylene Glycol | 1.5% |
| Sodium Cocoamphoacetate | 1.0% |
| Glycol Distearate | 0.8% |
| Lauramide MIPA | 0.5% |
| C12-14 Hydroxyalkyl Hydroxyethyl Sarcosine | 0.5% |
| Dimethicone | 0.4% |
| Polyquaternium-10 | 0.2% |
| Polyquaternium-7 | 0.1% |
| Sodium Citrate | 0.1% |
| Hydrolyzed Collagen | 0.1% |
| Laureth-25 | 0.1% |
| *Rosa Canina* Fruit Oil | 0.1% |

TABLE 27-continued

Shampoo

| | |
|---|---|
| Disodium EDTA | 0.1% |
| Citric Acid | ad pH 5.5 |
| Preservative, perfume | q.s. |

TABLE 28

Shower gel

| | |
|---|---|
| Water | ad 100% |
| Product example 1b: Sophorolipid + 10% oleic acid | 4.2% |
| Sodium Laureth Sulfate | 4.0% |
| Cocamidopropyl Betaine | 2.5% |
| Glycerin | 2.0% |
| Sodium Chloride | 1.5% |
| Sodium Myristoyl Sarcosinate | 1.2% |
| *Prunus Cerasus* Juice | 0.7% |
| Caramel | 0.2% |
| Disodium EDTA | 0.1% |
| Propylene Glycol | 0.2% |
| PEG-120 Methyl Glucose Trioleate | 0.3% |
| Citric Acid | ad pH 5.5 |
| Preservative, perfume | q.s. |

TABLE 29

Shower gel

| | |
|---|---|
| Water | ad 100% |
| Ammonium Laureth Sulfate | 5.5% |
| Cocamidopropyl Betaine | 2.5% |
| Product example 1b: Sophorolipid + 10% oleic acid | 1.5% |
| Sorbitol | 1.2% |
| Cocamide Methyl MEA | 0.7% |
| PEG-7 Glyceryl Cocoate | 0.6% |
| Sodium Cocoyl Alaninate | 0.8% |
| Sodium Chloride | 0.7% |
| DMDM Hydantoin | 0.1% |
| Disodium EDTA | 0.1% |
| *Santalum Album* Extract (Extract) | 0.1% |
| Lactic Acid, 90% | ad pH 5.5 |
| Preservative, perfume | q.s. |

TABLE 30

Hand cleaning paste

| | |
|---|---|
| Water | ad 100% |
| Laureth-5 | 5.0% |
| *Juglans Regia* | 3.0% |
| Sodium Laureth Sulfate | 5.0% |
| Product example 1b: Sophorolipid + 10% oleic acid | 2.0% |
| Bentonite | 1.0% |
| Sodium Cocoamphoacetate | 0.7% |
| Oleic Acid | 0.5% |
| C12-13 Alkyl Lactate | 0.5% |
| *Aloe Barbadensis* | 0.3% |
| Sodium Chloride | 0.3% |
| PEG-14M | 0.2% |
| Citric Acid | ad pH 6.0 |
| Preservative, perfume | q.s. |

TABLE 31

Shower oil

| | |
|---|---|
| Glycerin Soya Oil | 40.0% |
| Lecithin | 20.0% |
| MIPA-Laureth Sulfate | 4.0% |
| Product example 1b: Sophorolipid + 10% oleic acid | 4.0% |

TABLE 31-continued

Shower oil

| | |
|---|---|
| Laureth-4 | 3.0% |
| Cocamide DEA | 1.0% |
| Poloxamer 101 | 1.0% |
| *Persea Gratissima* Oil | 1.0% |
| Sodium Lactate | 0.5% |
| Water | ad 100% |
| Caprylic/Capric Triglyceride | 0.7% |
| Ascorbyl Palmitate | 0.5% |
| Sodium Citrate | 0.5% |
| Preservative, perfume | q.s. |

Alkyl Sulphate-Based Systems:

TABLE 32

Care shower

| | |
|---|---|
| Water | ad 100% |
| Ammonium Lauryl Sulfate | 5.0% |
| Lauryl Glucoside | 3.0% |
| Cocamidopropyl Betaine | 2.5% |
| Product example 1b: Sophorolipid + 10% oleic acid | 2.0% |
| Lauroyl Sarcosine | 0.7% |
| *Bambusa Arundinacea* Extract | 1.0% |
| *Citrus Grandis* Extract | 1.0% |
| Alcohol | 0.7% |
| Hydroxypropyl Guar Hydroxypropyltrimonium Chloride | 0.3% |
| *Citrus Medica Limonum* Oil | 0.3% |
| Preservative, perfume | q.s. |

TABLE 33

Baby washing lotion and shampoo

| | |
|---|---|
| Water | ad 100% |
| Sodium Coco Sulfate | 5.5% |
| Glycerin | 3.5% |
| Product example 1b: Sophorolipid + 10% oleic acid | 3.0% |
| Decyl Glucoside | 1.5% |
| Alcohol | 1.0% |
| Xanthan Gum | 1.0% |
| *Bellis Perennis* Extract | 0.7% |
| *Arnica Montana* Extract | 0.7% |
| *Chamomilla Recutita* Extract | 0.5% |
| Disodium Cocoyl Glutamate | 0.5% |
| Sodium Cocoyl Glutamate | 0.3% |
| Preservative, perfume | q.s. |

TABLE 34

Shampoo

| | |
|---|---|
| Water | ad 100% |
| Ammonium Lauryl Sulfate | 3.0% |
| Ammonium Laureth Sulfate | 2.5% |
| Cocamidopropyl Betaine | 2.0% |
| Product example 2b: Rhamnolipid + 10% oleic acid | 1.5% |
| Sodium Cocoyl Isethionate | 1.0% |
| Ammonium Chloride | 0.8% |
| Sodium Methyl Cocoyl Taurate | 0.7% |
| Sodium Lauroamphoacetate | 0.5% |
| Glycol Distearate | 0.5% |
| Laureth-7 | 0.4% |
| Propylene Glycol | 0.4% |
| Guar Hydroxypropyltrimonium Chloride | 0.2% |
| Dipropylene Glycol | 0.2% |
| Tetrasodium EDTA | 0.1% |
| Sodium Xylene Sulfonate | 0.1% |
| PEG-20 Castor Oil | 0.2% |
| Sodium Cocoamphoacetate | 0.2% |
| Quaternium-80 | 0.3% |
| *Persea Gratissima* Oil | 0.3% |

TABLE 34-continued

Shampoo

| | |
|---|---|
| Citric Acid, 30% | ad pH 5.5 |
| Preservative, perfume | q.s. |

Betaine-Based Systems:

TABLE 35

Mild, sulphate-free hair and body cleanser

| | |
|---|---|
| Cocamidopropyl Betaine | 5.0% |
| Sodium Cocoamphoacetate | 4.0% |
| Product example 2b: Rhamnolipid + 10% oleic acid | 1.5% |
| Sucrose Cocoate | 1.5% |
| PEG-120 Methyl Glucose Dioleate | 2.0% |
| Polyquaternium-10 | 0.2% |
| Water | ad 100% |
| Citric Acid, 30% | ad pH 6.0 |
| Preservative, perfume, dyes | q.s. |

TABLE 36

Mild, PEG-free hair and body cleanser

| | |
|---|---|
| Water | ad 100% |
| Cocamidopropyl Betaine | 5.5% |
| Lauryl Glucoside | 3.0% |
| Sodium Cocoamphoacetate | 3.0% |
| Product example 1b: Sophorolipid + 10% oleic acid | 1.5% |
| Hydroxypropyl Methylcellulose | 0.5% |
| Isostearamide MIPA (and) Glyceryl Laurate | 1.4% |
| Polyquaternium-7 | 0.5% |
| Citric Acid, 30% | ad pH 5.0 |
| Perfume, preservative | q.s. |

TABLE 37

Care shower for sensitive skin

| | |
|---|---|
| Water | ad 100% |
| Cocamidopropyl Betaine | 5.0% |
| Sodium Myreth Sulfate | 3.0% |
| Sodium Laureth Sulfate | 1.5% |
| Product example 1b: Sophorolipid + 10% oleic acid | 1.5% |
| PEG-7 Glyceryl Cocoate | 1.5% |
| Glycerin | 1.0% |
| Glyceryl Glucoside | 1.0% |
| Bisabolol | 0.3% |
| *Chamamilla Recutica* Flower Extract | 0.3% |
| Sodium Chloride | 0.3% |
| PEG-40 Hydrogenated Castor Oil | 0.3% |
| Polyquaternium-7 | 0.3% |
| PEG-90 Glyceryl Isostearate | 0.3% |
| PEG-200 Hydrogenated Glyceryl Palmate | 0.3% |
| Benzophenone-4 | 0.1% |
| Laureth-2 | 0.1% |
| Citric Acid | ad pH 4.9 |
| Preservative, perfume | q.s. |

TABLE 38

Baby Shampoo

| | |
|---|---|
| Water | ad 100% |
| Cocamidopropyl Betaine | 6.0% |
| PEG-80 Sorbitan Laurate | 3.0% |
| Product example 2b: Rhamnolipid + 10% oleic acid | 2.0% |
| Sodium Trideceth Sulfate | 1.5% |
| PEG-150 Distearate | 1.5% |
| Tetrasodium EDTA | 0.5% |

TABLE 38-continued

Baby Shampoo

| | |
|---|---|
| Polyquaternium-10 | 0.2% |
| Quaternium-15 | 0.2% |
| Sodium Hydroxide | 0.3% |
| Citric Acid | ad pH 5.9 |
| Preservative, perfume, dyes | q.s. |

TABLE 39

Baby Shampoo

| | |
|---|---|
| Water | ad 100% |
| Cocamidopropyl Betaine | 7.0% |
| Product example 1b: Sophorolipid + 10% oleic acid | 2.5% |
| Sodium Laureth Sulfate | 1.5% |
| PEG-120 Methyl Glucose Dioleate | 1.0% |
| Coco Glucoside | 1.0% |
| Glyceryl Oleate | 0.7% |
| Quaternium-22 | 0.3% |
| C12-15 Alkyl Lactate | 0.2% |
| Quaternium-26 | 0.2% |
| Citric Acid | ad pH 5.5 |
| Preservative, perfume, dyes | q.s. |

TABLE 40

Baby Shampoo

| | |
|---|---|
| Water | ad 100% |
| PEG-80 Sorbitan Laurate | 3.5% |
| Cocamidopropyl Betaine | 3.5% |
| Sodium Trideceth Sulfate | 3.5% |
| Glycerin | 1.0% |
| Product example 1b: Sophorolipid + 10% oleic acid | 0.9% |
| Lauroamphoglycinate | 0.7% |
| PEG-150 Distearate | 0.5% |
| Sodium Laureth-13 Carboxylate | 0.5% |
| Sodium *Amygdalus Dulcis* Extract | 0.3% |
| Polyquaternium-10 | 0.2% |
| Tetrasodium EDTA | 0.1% |
| Quaternium-15 | 0.1% |
| Citric Acid | ad pH 5.2 |
| Preservative, perfume, dyes | q.s. |

TABLE 41

Shampoo

| | |
|---|---|
| Water | ad 100% |
| Cocamidopropyl Betaine | 4.0% |
| Sodium Lauryl Sulfoacetate | 3.0% |
| Product example 1b: Sophorolipid + 10% oleic acid | 2.0% |
| Disodium Laureth Sulfosuccinate | 1.0% |
| Sodium Lauroyl Sarcosinate | 1.0% |
| Glycol Distearate | 0.9% |
| Sodium Chloride | 0.9% |
| Decyl Glucoside | 0.5% |
| Polyquaternium-10 | 0.3% |
| PPG-5-Ceteth-20 | 0.5% |
| Coco-Betaine | 0.5% |
| PEG-55 Propylene Glycol Oleate | 0.4% |
| Propylene Glycol | 0.3% |
| Salicylic Acid | 0.2% |
| Carbomer | 0.3% |
| Sodium Hydroxide | 0.2% |
| Citric Acid | ad pH 5.5 |
| Preservative, perfume, dyes | q.s. |

Amphoacetate-Based Systems:

TABLE 42

Body cleanser, PEG- & sulphate-free

| | |
|---|---|
| Water | ad 100% |
| Sodium Cocoamphoacetate | 5.0% |
| Disodium Lauryl Sulfosuccinate | 1.2% |
| Product example 1b: Sophorolipid + 10% oleic acid | 2.5% |
| Cocamidopropyl Betaine | 3.0% |
| Cocamidopropyl Betaine (and) Glyceryl Laurate | 1.0% |
| Citric Acid, 30% | ad pH 5.0 |
| Preservative, perfume | q.s. |

TABLE 43

Shampoo, PEG- & sulphate-free

| | |
|---|---|
| Water | ad 100% |
| Sodium Cocoamphoacetate | 5.5% |
| Disodium Cocoyl Glutamate | 2.0% |
| Product example 2b: Rhamnolipid + 10% oleic acid | 2.0% |
| Polyquaternium-10 | 0.2% |
| Palmitamidopropyltrimonium Chloride | 1.0% |
| Isostearamide MIPA | 1.0% |
| Citric Acid, 30% | ad pH 5.5 |
| Preservative, perfume | q.s. |

TABLE 44

Hair & body cleanser, PEG- and sulphate-free

| | |
|---|---|
| Sodium Cocoamphoacetate | 3.5% |
| Product example 2b: Rhamnolipid + 10% oleic acid | 3.5% |
| Disodium Lauryl Sulfosuccinate | 1.5% |
| Sorbitan Sesquicaprylate | 0.9% |
| Water | ad 100% |
| Cocamidopropyl Betaine | 3.0% |
| Citric Acid, 30% | ad pH 5.5 |
| Preservative, perfume | q.s. |

TABLE 45

Mild face cleansing gel, PEG- and sulphate-free, Ecocert-conform

| | |
|---|---|
| Water | ad 100% |
| Xanthan Gum | 1.5% |
| Sodium Cocoamphoacetate | 3.0% |
| Product example 1b: Sophorolipid + 10% oleic acid | 2.5% |
| Cocamidopropyl Betaine | 2.0% |
| Capryl/Capramidopropyl Betaine | 2.0% |
| Sucrose Cocoate | 0.6% |
| Polyglyceryl-3 Caprate | 3.0% |
| Cocamidopropyl Betaine (and) Glyceryl Laurate | 1.3% |
| NaCl | 1.5% |
| Citric Acid, 30% | ad pH 5.0 |
| Preservative, perfume | q.s. |

TABLE 46

Body cleanser

| | |
|---|---|
| Water | ad 100% |
| Glycerin | 5.0% |
| *Helianthus Annuus* Hybrid Oil | 3.5% |
| Cocamidopropyl Betaine | 3.5% |
| Sodium Hydroxypropyl Starch Phosphate | 3.0% |
| Sodium Laureth Sulfate | 3.0% |
| Sodium Cocoyl Glycinate | 2.5% |
| Product example 2b: Rhamnolipid + 10% oleic acid | 2.5% |
| Lauric Acid | 1.0% |

TABLE 46-continued

Body cleanser

| | |
|---|---|
| Sodium Lauroyl Isethionate | 1.0% |
| Stearic Acid | 0.5% |
| Sodium Palmitate | 0.5% |
| Sodium Chloride | 0.5% |
| Guar Hydroxypropyltrimonium Chloride | 0.2% |
| Sodium Stearate | 0.2% |
| Tetrasodium EDTA | 0.1% |
| Tetrasodium Etidronate | 0.1% |
| Alumina | 0.1% |
| Citric Acid, 30% | ad pH 6.1 |
| Preservative, perfume, dyes | q.s. |

APG-Based Systems:

TABLE 47

Mild hair and body cleanser

| | |
|---|---|
| Water | ad 100% |
| Lauryl Glucoside | 5.0% |
| Coco Glucoside | 2.0% |
| Product example 2b: Rhamnolipid + 10% oleic acid | 3.0% |
| Sucrose Cocoate | 1.5% |
| Cocamidopropyl Betaine | 4.0% |
| Carbomer | 1.0% |
| Citric Acid, 30% | ad pH 5.5 |
| Preservative, perfume | q.s. |

TABLE 48

Pampering shower

| | |
|---|---|
| Water | ad 100% |
| *Sesamum Indicum* (Sesame) Seed Oil | 5.0% |
| Coco Glucoside | 5.0% |
| Alcohol | 5.0% |
| Product example 2b: Rhamnolipid + 10% oleic acid | 3.0% |
| Disodium Cocoyl Glutamate | 3.0% |
| Glycerin | 2.5% |
| *Rosa Moschata* Seed Oil | 0.5% |
| Xanthan Gum | 0.7% |
| Lactic Acid, 90% | ad pH 5.5 |
| Perfume | q.s. |

TABLE 49

Shower & bath gel

| | |
|---|---|
| Water | ad 100% |
| Glycerin | 6.0% |
| Coco Glucoside | 5.5% |
| Caprylyl/Capryl Glucoside | 5.0% |
| Product example 1b: Sophorolipid + 10% oleic acid | 2.0% |
| Sodium Coco-Sulfate | 3.5% |
| *Prunus Armeniaca* (Apricot) Fruit Extract | 2.0% |
| Xanthan Gum | 2.0% |
| Alcohol | 1.0% |
| Perfume | q.s. |

TABLE 50

Shower gel

| | |
|---|---|
| Water | ad 100% |
| Coco Glucoside | 7.0% |
| Sodium Coco Sulfate | 4.0% |
| Lauryl Glucoside | 2.0% |
| Product example 1b: Sophorolipid + 10% oleic acid | 2.0% |
| Glyceryl Oleate | 2.0% |

TABLE 50-continued

Shower gel

| | |
|---|---|
| Glycerin | 2.0% |
| Inulin | 0.5% |
| *Aloe Barbadensis* Leaf Juice | 0.4% |
| Sorbitol | 0.4% |
| Betaine | 0.2% |
| Sodium Cocoyl Glutamate | 0.2% |
| Disodium Cocoyl Glutamate | 0.2% |
| *Cocos Nucifera* (Coconut) Fruit Extract | 0.1% |
| Maris Sal | 0.1% |
| Glyceryl Caprylate | 0.1% |
| Sodium PCA | 0.1% |
| PCA Ethyl Cocoyl Arginate | 0.1% |
| Potassium Sorbate | 0.9% |
| Citric Acid | ad pH 5.5 |
| Perfume | q.s. |

TABLE 51

Kids' foam bath

| | |
|---|---|
| Water | ad 100% |
| Product example 1b: Sophorolipid + 10% oleic acid | 4.0% |
| Lauryl Glucoside | 4.0% |
| *Aloe Barbadensis* Leaf Extract | 4.0% |
| Sodium Lauryl Sulfoacetate | 2.0% |
| Glycerin | 2.0% |
| Polyglyceryl-10 Laurate | 2.0% |
| Coco Glucoside | 2.0% |
| Glyceryl Oleate | 0.5% |
| Disodium Cocoyl Glutamate | 0.4% |
| Sodium Cocoyl Glutamate | 0.4% |
| *Calendula Officinalis* Flower Extract | 0.2% |
| Sodium Chloride | 0.2% |
| Citric Acid | ad pH 5.5 |
| Perfume | q.s. |

TABLE 52

Shower gel

| | |
|---|---|
| Water | ad 100% |
| Product example 2b: Rhamnolipid + 10% oleic acid | 4.0% |
| Coco Glucoside | 4.0% |
| Glycerin | 3.0% |
| Disodium Cocoyl Glutamate | 2.0% |
| Sodium Cocoyl Glutamate | 2.0% |
| Polyglyceryl-10 Laurate | 1.0% |
| Glyceryl Caprylate | 1.0% |
| *Rubus Idaeus* (Raspberry) Fruit Extract | 0.3% |
| Sodium PCA | 0.2% |
| Xanthan Gum | 0.6% |
| Glyceryl Oleate | 0.3% |
| Phytic Acid | 0.1% |
| Citric Acid | ad pH 5.5 |
| Perfume | q.s. |

TABLE 53

Ultra sensitive shower cream

| | |
|---|---|
| Water Aqua | ad 100% |
| Coco Glucoside | 7.0% |
| Alcohol | 3.0% |
| Product example 1b: Sophorolipid + 10% oleic acid | 3.0% |
| Glycerin | 2.5% |
| *Simmondsia Chinensis* Seed Oil | 1.5% |
| Xanthan Gum | 1.3% |
| Disodium Cocoyl Glutamate | 1.0% |
| Glyceryl Oleate | 0.8% |
| Sodium Cocoyl Glutamate | 0.5% |

TABLE 53-continued

Ultra sensitive shower cream

| | |
|---|---|
| Citric Acid | ad pH 5.5 |
| Preservative, perfume | q.s. |

TABLE 54

Antidandruff shampoo

| | |
|---|---|
| Water | ad 100% |
| Sorbitol | 5.5% |
| Glycerin | 5.0% |
| Coco Glucoside | 4.5% |
| Product example 1b: Sophorolipid + 10% oleic acid | 3.5% |
| Loess | 1.0% |
| *Zea Mays* Oil | 1.0% |
| Sodium Lauroyl Lactylate | 1.5% |
| Sodium Cocoyl Glutamate | 1.0% |
| Disodium Cocoyl Glutamate | 1.0% |
| Xanthan Gum | 0.7% |
| Kaolin | 0.3% |
| Canola Oil | 0.3% |
| Sodium Coco-Glucoside Tartrate | 0.2% |
| Tocopherol | 0.1% |
| Citric Acid | ad pH 5.3 |
| Preservative, perfume | q.s. |

TABLE 55

Mild hair & body cleanser, ECOCERT ingredients

| | |
|---|---|
| Lauryl Glucoside | 3.0% |
| Product example 1b: Sophorolipid + 10% oleic acid | 2.0% |
| Cocamidopropyl Betaine (and) Glyceryl Laurate | 5.0% |
| Sorbitan Sesquicaprylate | 0.9% |
| Water | ad 100% |
| Cocamidopropyl Betaine | 4.0% |
| Citric Acid, 30% | ad pH 5.5 |
| Preservative, perfume | q.s. |

TABLE 56

Mild cleansing foam

| | |
|---|---|
| Water | ad 100% |
| *Glycine Soya* Oil | 8.0% |
| Glycerin | 5.0% |
| Alcohol | 5.0% |
| Product example 2b: Rhamnolipid + 10% oleic acid | 4.0% |
| Coco Glucoside | 3.5% |
| Caprylic/Capric Triglyceride | 2.0% |
| Sodium Coco Sulfate | 2.0% |
| Sodium Lactate | 1.0% |
| Sodium Cocoyl Glutamate | 1.0% |
| Disodium Cocoyl Glutamate | 0.6% |
| *Argania Spinosa* Kernel Oil | 0.6% |
| Preservative, perfume | q.s. |

TABLE 57

Washing gel

| | |
|---|---|
| Water | ad 100% |
| Alcohol | 7.0% |
| Glycerin | 5.5% |
| Coco Glucoside | 4.0% |
| Product example 1b: Sophorolipid + 10% oleic acid | 3.0% |
| Sodium Cocoyl Glutamate | 2.0% |
| Xanthan Gum | 2.0% |
| *Equisetum Arvense* Leaf Extract | 1.0% |
| Disodium Cocoyl Glutamate | 0.4% |

TABLE 57-continued

Washing gel

| | |
|---|---|
| Citric Acid | ad pH 5.5 |
| Preservative, perfume | q.s. |

TABLE 58

Mild hair & body cleanser, PEG- and sulphate-free

| | |
|---|---|
| Lauryl Glucoside | 3.5% |
| Product example 1b: Sophorolipid + 10% oleic acid | 2.0% |
| Isostearamide MIPA (and) Glyceryl Laurate | 1.0% |
| Water | ad 100% |
| Coco Glucoside | 1.0% |
| Sodium Cocoamphoacetate | 3.0% |
| Cocoamidopropyl Betaine | 3.5% |
| Citric Acid, 30% | ad pH 5.5 |
| Preservative, perfume | q.s. |

TABLE 59

Wet wipes

| | |
|---|---|
| Water | ad 100% |
| Caprylyl/Capryl Glucoside | 3.0% |
| Product example 2b: Rhamnolipid + 10% oleic acid | 3.5% |
| Coco Glucoside | 2.5% |
| Polyaminopropyl Biguanide | 1.0% |
| Propylene Glycol | 1.0% |
| Simethicone | 0.5% |
| *Aloe Barbadensis* Extract | 0.3% |
| Citric Acid | ad pH 5.7 |
| Preservative, perfume | q.s. |

TABLE 60

Bio shower bath

| | |
|---|---|
| Water | ad 100% |
| Glycerin | 4.0% |
| Lauryl Glucoside | 4.0% |
| Product example 2b: Rhamnolipid + 10% oleic acid | 3.5% |
| Ammonium Lauryl Sulfate | 3.0% |
| Cocamidopropyl Betaine | 2.0% |
| Lauroyl Sarcosine | 1.0% |
| Hydroxypropyl Guar Hydroxypropyltrimonium Chloride | 0.3% |
| Alcohol | 0.3% |
| Preservative, perfume, dyes | q.s. |

TABLE 61

Baby shampoo

| | |
|---|---|
| Water | ad 100% |
| Coco-Glucoside | 4.5% |
| Sodium Lauroamphoacetate | 3.5% |
| Sodium Laureth Sulfate | 2.5% |
| Product example 1b: Sophorolipid + 10% oleic acid | 2.5% |
| Citric Acid | ad pH 5.5 |
| Polysorbate 20 | 0.7% |
| PEG-80 Sorbitan Laurate | 0.5% |
| PEG-150 Distearate | 0.3% |
| Polyquaternium-10 | 0.3% |
| Butylene Glycol | 0.2% |
| Propylene Glycol | 0.2% |
| Lactic Acid | 0.2% |
| Glucose | 0.1% |
| Preservative, perfume, dyes | q.s. |

TABLE 62

Mild body cleanser

| | |
|---|---|
| Water | ad 100% |
| Lauryl Glucoside | 3.5% |
| Sorbitan Sesquicaprylate | 0.6% |
| Coco Glucoside | 0.5% |
| Product example 2b: Rhamnolipid + 10% oleic acid | 1.5% |
| Disodium Lauryl Sulfosuccinate | 2.0% |
| Cocamidopropyl Betaine | 3.5% |
| Citric Acid, 30% | 1.5% |
| Preservative, perfume | q.s. |

TABLE 63

Shower gel

| | |
|---|---|
| Water | ad 100% |
| Lauryl Glucoside | 8.0% |
| Cocamidopropyl Betaine | 2.5% |
| Product example 1b: Sophorolipid + 10% oleic acid | 2.5% |
| Dimethicone Propyl PG-Betaine | 0.3% |
| PEG-7 Glyceryl Cocoate | 2.0% |
| PEG-18 Glyceryl Oleate/Cocoate | 2.0% |
| Preservative, perfume | q.s. |

TABLE 64

Mild body cleanser, Ecocert-conform, PEG-, sulphate- and betaine-free

| | |
|---|---|
| Water | ad 100% |
| Lauryl Glucoside | 4.0% |
| Product example 2b: Rhamnolipid + 10% oleic acid | 0.9% |
| Sorbitan Sesquicaprylate | 0.6% |
| Coco Glucoside, Cognis | 1.0% |
| Sodium/Disodium Cocoyl Glutamate | 2.0% |
| Sodium Cocoamphoacetate | 3.0% |
| Citric Acid | ad pH 5.1 |
| Preservative, perfume | q.s. |

Sulphonate-Based Systems:

TABLE 65

Sulphate-free shampoo with MHEC

| | |
|---|---|
| Water | ad 100% |
| Sodium C14-16 Olefin Sulfonate | 4.0% |
| Product example 2b: Rhamnolipid + 10% oleic acid | 3.0% |
| Cocoamidopropyl Betaine | 3.0% |
| Methylhydroxyethylcellulose | 1.5% |
| Preservative, perfume | q.s. |

TABLE 66

Oil-free acne cleanser

| | |
|---|---|
| Water | ad 100% |
| Sodium C14-16 Olefin Sulfonate | 4.0% |
| Cocamidopropyl Betaine | 3.0% |
| Product example 1b: Sophorolipid + 10% oleic acid | 2.5% |
| Sodium C12-15 Pareth-15 Sulfonate | 2.5% |
| *Aloe* Extract | 1.0% |
| Camomile Extract | 1.0% |
| Linoleamidopropyl PG-Dimonium Chloride Phosphate | 0.7% |
| Disodium-EDTA | 0.2% |
| Propylene Glycol | 0.3% |
| Salicylic Acid | 2.0% |
| Sodium Choride | 1.0% |
| Preservative, perfume, dyes | q.s. |

TABLE 67

Washing emulsion for sensitive and problematic skin

| | |
|---|---|
| Water | ad 100% |
| Sodium C14-16 Olefin Sulfonate | 4.0% |
| Sodium Laureth Sulfate | 3.0% |
| Product example 1b: Sophorolipid + 10% oleic acid | 2.0% |
| Disodium Laureth Sulfosuccinate | 1.5% |
| Sodium Chloride | 2.0% |
| Laureth-2 | 1.0% |
| Panthenol | 0.5% |
| Glycol Distearate | 0.5% |
| Saccharide Isomerate | 0.2% |
| Allantoin | 0.2% |
| Niacinamide | 0.1% |
| Pyridoxine HCl | 0.1% |
| Glycine | 0.1% |
| Alanine | 0.1% |
| Lysine | 0.1% |
| Biotin | 0.1% |
| Glycerin | 0.5% |
| Sodium Lauroyl Glutamate | 0.5% |
| Sodium Citrate | 0.5% |
| Cocamidopropyl Betaine | 0.5% |
| Sorbitan Laurate | 0.4% |
| PEG-120 Methyl Glucose Dioleate | 0.3% |
| Preservative, perfume | q.s. |

Sulphosuccinate-Based Systems:

TABLE 68

Kids' shower & shampoo

| | |
|---|---|
| Water | ad 100% |
| Disodium Laureth Sulfosuccinate | 4.5% |
| Product example 2b: Rhamnolipid + 10% oleic acid | 3.5% |
| Cocamidopropyl Hydroxysultaine | 2.5% |
| Cocamidopropyl Betaine | 1.5% |
| Decyl Glucoside | 1.0% |
| PEG-18 Glyceryl Oleate/Cocoate | 0.7% |
| Laureth-2 | 0.5% |
| Sodium Chloride | 0.5% |
| Panthenol | 0.2% |
| Niacinamide | 0.1% |
| Pyridoxan Hydrochloride | 0.1% |
| Polyquaternium-10 | 0.3% |
| Glycerin | 0.3% |
| Inulin | 0.1% |
| Citric Acid | ad pH 5.7 |
| Preservative, perfume, dyes | q.s. |

TABLE 69

Mild baby shampoo

| | |
|---|---|
| Water | ad 100% |
| Disodium Laureth Sulfosuccinate | 3.5% |
| Product example 1b: Sophorolipid + 10% oleic acid | 3.5% |
| Isostearamide MIPA (and) Glyceryl Laurate | 1.7% |
| PEG-7 Glyceryl Cocoate | 0.5% |
| Sodium Cocoamphoacetate | 3.0% |
| Palmitamidopropyltrimonium Chloride | 2.3% |
| Citric Acid, 30% | ad pH 6.0 |
| Preservative, perfume, dyes | q.s. |

TABLE 70

Mild face cleansing foam

| | |
|---|---|
| Water | ad 100% |
| Disodium PEG-5 Laurylcitrate Sulfosuccinate (and) Capryl/Capramidopropyl Betaine | 5.5% |
| Product example 1b: Sophorolipid + 10% oleic acid | 3.0% |
| Capryl/Capramidopropyl Betaine | 2.0% |

TABLE 70-continued

Mild face cleansing foam

| | |
|---|---|
| Polyglyceryl-3 Caprate | 0.5% |
| Creatine | 0.2% |
| Hydroxypropyl Methylcellulose | 0.5% |
| Sodium Lactate (and) Sodium PCA (and) Glycine (and) Fructose (and) Urea (and) Niacinamide (and) Inositol (and) Sodium Benzoate (and) Lactic Acid | 1.0% |
| Preservative, perfume | q.s. |

Sarcosinate-Based Systems:

TABLE 71

Shampoo

| | |
|---|---|
| Water | ad 100% |
| Sodium Lauroyl Sarcosinate | 5.0% |
| Coco Betaine | 3.0% |
| Product example 2b: Rhamnolipid + 10% oleic acid | 1.5% |
| Cocamide DEA | 4.5% |
| Cetrimonium Chloride | 0.3% |
| Steralkonium Chloride | 0.1% |
| Disodium EDTA | 0.2% |
| Citric Acid | ad pH 6.7 |
| Preservative, perfume | q.s. |

TABLE 72

Shampoo

| | |
|---|---|
| Water | ad 100% |
| Sodium Lauroyl Sarcosinate | 5.0% |
| Product example 1b: Sophorolipid + 10% oleic acid | 2.5% |
| Cocamidopropyl Betaine | 4.0% |
| Palmitamidopropyltrimonium Chloride | 0.5% |
| Polyquaternium-10 | 0.1% |
| Citric Acid | ad pH 5.1 |
| Preservative, perfume | q.s. |

TABLE 73

Shampoo

| | |
|---|---|
| Water | ad 100% |
| Sodium Lauroyl Sarcosinate | 3.5% |
| Product example 1b: Sophorolipid + 10% oleic acid | 3.5% |
| Sodium Cocoamphoacetate | 2.5% |
| Cocamidopropyl Betaine | 1.0% |
| Coco-Betaine | 1.0% |
| Coco-Glucoside | 0.5% |
| Glyceryl Oleate | 0.5% |
| Polyquaternium-7 | 0.3% |
| Polysorbate 20 | 0.2% |
| Silicone Quaternium-22 | 0.3% |
| PEG-120 Methyl Glucose Dioleate | 0.3% |
| *Hibiscus Sabdariffa* (Hibiscus) Extract | 0.1% |
| Glycerin | 0.2% |
| Sodium Hydroxymethylglycinate | 0.2% |
| Citric Acid | ad pH 5.1 |
| Preservative, perfume | q.s. |

TABLE 74

Mild body cleanser

| | |
|---|---|
| Water | ad 100% |
| Sodium Lauroyl Sarcosinate | 2.5% |
| Sodium Lauroamphoacetate | 2.5% |
| Sodium Cocoyl Alaninate | 2.0% |
| Product example 2b: Rhamnolipid + 10% oleic acid | 1.5% |

TABLE 74-continued

Mild body cleanser

| | |
|---|---|
| Sodium Cocoamphoacetate | 1.5% |
| Lauryl Glucoside | 1.5% |
| Disodium Cocoyl Glutamate | 0.5% |
| Sodium Lauryl Glucose Carboxylate | 0.5% |
| PEG-150 Distearate | 0.5% |
| Polysorbate 20 | 0.4% |
| Glycerin | 0.5% |
| Algae Extract | 0.1% |
| Methyl Gluceth-20 | 0.2% |
| Coco-glucoside | 0.3% |
| Glyceryl Oleate | 0.5% |
| Allantoin | 0.1% |
| PEG-40 Hydrogenated Castor Oil | 0.4% |
| Disodium EDTA | 0.1% |
| Citric Acid | ad pH 5.5 |
| Preservative, perfume | q.s. |

Other-Based Systems (Sultain, Anisate, Isethionate, Glutamate, Glycinate):

TABLE 75

Baby care bath

| | |
|---|---|
| Water | ad 100% |
| Sorbitol | 3.5% |
| Cocamidopropyl Hydroxysultaine | 3.5% |
| Product example 1b: Sophorolipid + 10% oleic acid | 3.0% |
| Cocamidopropyl Betaine | 2.5% |
| Lauryl Glucoside | 1.0% |
| Coco-Glucoside | 1.0% |
| Sodium Chloride | 1.5% |
| Glyceryl Oleate | 0.9% |
| Sodium *Amygdalus Dulcis* Extract | 0.3% |
| Sodium Carboxymethyl Betaglucan | 0.3% |
| Glycerin | 0.3% |
| Styrene/Acrylates Copolymer | 0.3% |
| Inulin | 0.1% |
| Preservative, perfume, dyes | q.s. |

TABLE 76

Wet cleansing wipes

| | |
|---|---|
| Water | ad 100% |
| Glycerin | 5.0% |
| Sodium Anisate | 3.5% |
| Sodium Levulinate | 3.5% |
| Product example 1b: Sophorolipid + 10% oleic acid | 3.0% |
| Glyceryl Caprylate | 1.0% |
| Tocopheryl Acetate | 0.5% |
| Sodium Citrate | 0.5% |
| Xanthan Gum | 0.5% |
| Hydrolyzed Milk Protein | 0.4% |
| *Prunus Armeniaca* Kernel Oil | 0.3% |
| Magnesium Stearate | 0.2% |
| Preservative, perfume | q.s. |

TABLE 77

Shower gel

| | |
|---|---|
| Water | ad 100% |
| Sodium Lauroyl Methyl Isethionate | 4.5% |
| Product example 1b: Sophorolipid + 10% oleic acid | 3.0% |
| Cocamidopropyl Betaine | 2.5% |
| Sodium Chloride | 2.5% |
| Glycerin | 1.5% |
| Polyglyceryl-4 Caprate | 0.6% |
| Sucrose Cocoate | 0.5% |
| Trisodium Ethylenediamine Disuccinate | 0.2% |

TABLE 77-continued

Shower gel

| | |
|---|---|
| Zinc Laurate | 0.1% |
| Salicylic Acid | 0.1% |
| Propylene Glycol | 0.1% |
| *Aloe Barbadensis* Leaf Juice | 0.1% |
| Sodium Hydroxide | 0.1% |
| Tocopherol | 0.1% |
| Citric Acid | ad pH 5.5 |
| Preservative, perfume | q.s. |

TABLE 78

Shampoo

| | |
|---|---|
| Water | ad 100% |
| Sodium Cocoyl Isethionate | 3.0% |
| Product example 2b: Rhamnolipid + 10% oleic acid | 3.0% |
| Cocamidopropyl Hydroxysultaine | 3.0% |
| Cocamide DEA | 2.5% |
| Sodium Lauroyl Methyl Isethionate | 2.0% |
| Inulin | 1.0% |
| Sodium Cocoyl Glutamate | 0.7% |
| Sodium Lauroyl Glutamate | 0.7% |
| Hydrolyzed Wheat Protein | 0.4% |
| Hydroxypropyl Guar Hydroxypropyltrimonium Chloride | 0.1% |
| Polyquaternium-10 | 0.1% |
| *Arnica Montana* Flower Extract | 0.1% |
| Styrene/Acrylates Copolymer | 0.2% |
| Disodium EDTA | 0.1% |
| Sodium Hydroxide | 0.1% |
| Lactic Acid, 90% | ad pH 5.5 |
| Preservative, perfume | q.s. |

TABLE 79

Baby cleanser

| | |
|---|---|
| Water | ad 100% |
| Glycerin | 4.5% |
| Product example 1b: Sophorolipid + 10% oleic acid | 3.5% |
| Pentylene Glycol | 3.0% |
| Sodium Cocoamphoacetate | 3.0% |
| Cocamidopropyl Betaine | 3.0% |
| *Helianthus Annuus* Seed Oil | 1.6% |
| Lauryl Glucoside | 1.5% |
| Sodium PEG-7 Olive Oil Carboxylate | 0.5% |
| Hydroxyethylcellulose | 0.5% |
| Sodium Cocoyl Glutamate | 0.5% |
| Sodium Lauryl Glucose Carboxylate | 0.5% |
| Sodium Cocoa Butter Amphoacetate | 0.3% |
| Preservative, perfume | q.s. |

TABLE 80

Body and hair cleansing foam

| | |
|---|---|
| Water | ad 100% |
| Sodium Cocoyl Glutamate | 5.0% |
| Glycerin | 3.0% |
| Sodium Laureth Sulfate | 3.0% |
| Product example 2b: Rhamnolipid + 10% oleic acid | 2.0% |
| Pentylene Glycol | 2.0% |
| Sodium Cocoyl Alaninate | 1.0% |
| PEG-200 Hydrogenated Glyceryl Palmate (and) PEG-7 Glyceryl Cocoate | 1.2% |
| PEG-60 Glyceryl Isostearate | 0.5% |
| Cocamidopropyl PG-dimonium Chloride Phosphate | 0.3% |
| Butylene Glycol | 0.3% |
| Propylene Glycol | 0.5% |
| *Ginkgo Biloba* Leaf Extract | 0.1% |
| Tetrasodium EDTA | 0.1% |
| Benzophenone-4 | 0.2% |
| Citric Acid | ad pH 5.3 |
| Preservative, perfume, dyes | q.s. |

TABLE 81

Make-up remover

| | |
|---|---|
| Water | ad 100% |
| PEG-8 | 5.0% |
| Isopentyldiol | 2.0% |
| PEG-20 Glyceryl Triisostearate | 2.0% |
| Glycerin | 2.0% |
| Hydrogenated Polyisobutene | 2.0% |
| Potassium Cocoyl Glycinate | 2.0% |
| Lauryl Hydroxysultaine | 2.0% |
| Product example 1b: Sophorolipid + 10% oleic acid | 2.0% |
| Butylene Glycol Laurate | 1.5% |
| Lauryl Glucoside | 1.5% |
| Alcohol | 0.5% |
| Disodium EDTA | 0.1% |
| Citric Acid | ad pH 5.5 |
| Preservative, perfume, dyes | q.s. |

TABLE 82

Foaming body cleanser

| | |
|---|---|
| Water | ad 100% |
| Sodium Cocoyl Glycinate | 6.0% |
| Product example 2b: Rhamnolipid + 10% oleic acid | 4.0% |
| Coco-betaine | 2.0% |
| Glycerin | 1.0% |
| Sodium Chloride | 1.0% |
| Acrylates/C10-30 Alkyl Acrylate Crosspolymer | 0.5% |
| Sodium Hydroxide | 0.4% |
| PEG-14M | 0.3% |
| Salicylic Acid | 0.1% |
| Polyquaternium-10 | 0.1% |
| Glycol Distearate | 0.2% |
| Citric Acid | ad pH 5.5 |
| Preservative, perfume, dyes | q.s. |

TABLE 83

Further formulation examples

| | I | II | III | IV | V | VI | VII | VIII | IX | X |
|---|---|---|---|---|---|---|---|---|---|---|
| Water | ad 100% | | | | | | | | | |
| Product example 1b: Sophorolipid + 10% oleic acid | 10.0% | — | 3.0% | 3.5% | — | 2.0% | — | 4.0% | — | 3.0% |
| Product example 2b: Rhamnolipid + 10% oleic acid | — | 12.0% | 5.5% | — | 7.0% | 2.0% | 5.5% | — | 3.5% | — |

TABLE 83-continued

Further formulation examples

| | I | II | III | IV | V | VI | VII | VIII | IX | X |
|---|---|---|---|---|---|---|---|---|---|---|
| Sodium Laureth Sulfate | — | — | — | 7.0% | — | — | — | 4.5% | — | — |
| Ammonium Lauryl Sulfate | — | — | — | — | 5.0% | — | — | — | 3.5% | — |
| Cocamidopropyl Betaine | — | — | — | — | — | 6.0% | — | 2.5% | — | 4.5% |
| Sodium Cocoamphoacetate | — | — | — | — | — | — | — | — | 3.5% | — |
| Coco Glucoside | — | — | — | — | — | — | 5.5% | — | — | 2.5% |
| Sucrose Cocoate | 0.5% | 1.0% | 1.0% | 1.0% | 1.0% | 0.5% | 1.0% | 1.0% | 1.0% | 1.0% |
| Hydroxypropyl Methylcellulose | 0.5% | — | — | — | — | 0.3% | — | — | — | 0.1% |
| Polyglyceryl-4 Caprate | — | — | 1.0% | — | — | — | — | — | — | — |
| Hydroxypropyl Guar Hydroxypropyltrimonium Chloride | 0.2% | 0.2% | 0.2% | 0.2% | 0.2% | 0.2% | 0.2% | 0.2% | 0.2% | 0.2% |
| Silicone Quaternium-22 | — | — | — | 0.5% | 0.5% | — | — | — | — | — |
| Amodimethicone | — | — | — | — | — | — | 0.5% | — | — | — |
| Glycol Distearate | — | — | 0.5% | — | 0.5% | — | — | — | 0.5% | 0.5% |
| Carbomer | 1.0% | — | — | — | 0.5% | — | — | — | 0.5% | — |
| Sodium Hydroxide, 25% | 1.5% | — | — | — | 0.8% | — | — | — | 0.7% | — |
| Isostearamide MIPA; Glyceryl Laurate | — | 1.5% | — | — | — | — | — | — | 1.0% | 0.5% |
| Sorbitan Sesquicaprylate | — | 0.5% | — | 0.5% | 0.5% | 1.2% | 1.0% | — | — | 1.3% |
| Sodium Chloride | 1.0% | 1.0% | — | 0.5% | — | 1.5% | — | 2.0% | 1.5% | — |
| PEG-200 Hydrogenated Glyceryl Palmate; PEG-7 Glyceryl Cocoate | — | — | — | 0.4% | — | — | — | 0.6% | — | — |
| Xanthan Gum | — | — | 1.2% | — | — | — | 1.0% | — | — | 0.5% |
| Panthenol | 0.1% | 0.1% | 0.1% | 0.1% | 0.1% | 0.1% | 0.1% | 0.1% | 0.1% | 0.1% |
| Citric Acid | ad pH 5.5 | | | | | | | | | |
| Preservative, perfume, dyes | q.s. | | | | | | | | | |

TABLE 84

Further formulation examples

| | XI | XII | XIII | XIV | XV | XVI | XVII | XVIII | XIX | XX |
|---|---|---|---|---|---|---|---|---|---|---|
| Water | ad 100% | | | | | | | | | |
| Product example 1b: Sophorolipid + 10% oleic acid | 8.0% | — | 9.0% | 3.0% | — | 5.0% | — | 6.5% | 1.7% | 1.5% |
| Product example 2b: Rhamnolipid + 10% oleic acid | — | 7.0% | — | 4.0% | 7.0% | — | 5.5% | — | 0.5% | — |
| Disodium Lauryl Sulfosuccinate | 5.0% | — | — | — | — | 2.0% | — | — | — | — |
| Sodium Lauryl Sulfate | — | — | — | — | — | — | — | — | — | 6.0% |
| Cocamidopropyl Betaine | — | 5.0% | — | — | — | — | 2.5% | — | 6.0% | 2.5% |
| Coco-Betaine | — | — | — | 2.0% | — | — | 2.0% | — | 1.0% | — |
| Lauryl Glucoside | — | — | — | — | 3.0% | 2.0% | — | 4.5% | 4.5% | — |
| Sodium Cocoyl Glutamate | — | — | 3.5% | — | 1.5% | 1.0% | — | — | — | — |
| Sodium Lauroyl Sarcosinate | — | — | — | 0.9% | — | 1.0% | 2.5% | — | — | — |
| Sodium Cocoyl Isethionate | — | — | — | — | — | — | — | — | — | 1.0% |
| Sucrose Cocoate | 0.5% | 1.0% | 0.3% | 1.0% | — | — | 1.0% | 1.0% | 0.1% | 0.5% |
| Polyglyceryl-3 Caprate | — | — | 1.0% | — | — | — | — | — | — | — |
| Alcohol | — | — | — | — | 0.3% | 0.1% | — | — | — | — |
| Glycerin | — | — | 0.5% | — | 5.0% | 2.0% | — | 3.5% | — | — |
| Polyquaternium-10 | 0.2% | 0.2% | 0.2% | 0.2% | 0.2% | 0.2% | 0.2% | 0.3% | 0.3% | 0.2% |
| Dimethicone | — | — | — | — | — | — | 0.5% | — | — | — |
| Hydrolyzed Wheat Protein | 0.2% | — | 0.1% | — | 0.1% | — | — | — | 0.1% | — |
| Glycol Distearate | — | — | 0.5% | — | 0.3% | — | 0.5% | — | — | — |
| Carbomer | 1.0% | — | — | — | 0.5% | — | — | — | — | — |
| Sodium Hydroxide, 10% | q.s | — | — | — | 2.5% | — | — | — | — | — |
| Isostearamide MIPA; Glyceryl Laurate | — | 1.5% | — | — | — | — | — | — | 1.5% | 1.2% |
| Cocamide DEA | — | 0.5% | — | 0.5% | — | 1.2% | 2.0% | — | — | 0.3% |
| Sodium Chloride | 1.0% | 1.0% | — | 0.5% | — | 1.5% | — | 2.0% | 0.3% | 0.2% |
| PEG-120 Methyl Glucose Dioleate | 0.3% | — | — | — | — | — | — | — | — | — |
| Xanthan Gum | — | — | 0.9% | — | 1.0% | 0.3% | — | 1.0% | — | — |
| Creatine | 0.5% | 0.1% | 0.1% | 0.1% | 0.1% | 0.1% | 0.1% | 0.1% | 0.1% | 0.1% |
| Citric Acid | ad pH 5.2 | | | | | | | | | |
| Preservative, perfume, dyes | q.s. | | | | | | | | | |

TABLE 85

| List of raw materials used: | |
|---|---|
| INCI name: | Trade name: |
| Fatty alcohols: | |
| Cetyl Alcohol | TEGO Alkanol 16, Evonik Industries AG, 100% |
| Thickeners/stabilizers: | |
| Carbomer | TEGO Carbomer 140, Evonik Industries AG, 100% |
| Hydroxyethylcellulose | Natrosol Hydroxyethylcellulose, Ashland Aqualon |
| Acrylates/C10-30 Alkyl Acrylate Crosspolymer | TEGO Carbomer 341 ER, Evonik Industries AG, 100% |
| Cocamide DEA | REWOMID DC 212 S, Evonik Industries AG, 100% |
| Cocamide MEA | REWOMID D 212, Evonik Industries AG, 100% |
| Isostearamide MIPA; Glyceryl Laurate | ANTIL SPA 80, Evonik Industries AG, 100% |
| Sorbitan Sesquicaprylate | ANTIL Soft SC, Evonik Industries AG, 100% |
| Laureth-4 | TEGO Alkanol L 4, Evonik Industries AG, 100% |
| PEG-60 Glyceryl Isostearate | Emalex GWIS-160N, Nihon Emulsion Company |
| PEG-150 Distearate | REWOPAL PEG 6000 DS, Evonik Industries AG, 100% |
| PEG-120 Methyl Glucose Dioleate | ANTIL 120 Plus, Evonik Industries AG, 100% |
| PEG-18 Glyceryl Oleate/Cocoate | ANTIL 171, Evonik Industries AG, 100% |
| PEG-200 Hydrogenated Glyceryl Palmate; PEG-7 Glyceryl Cocoate | REWODERM LI S 80, Evonik Industries AG, 100% |
| Xanthan Gum | Keltrol CG-SFT, CP Kelco, 100% |
| Pearlizing agents: | |
| PEG-3 Distearate | Cutina TS, BASF Cognis, 100% |
| Glycol Distearate | TEGIN G 1100, Evonik Industries AG, 100% |
| Glycol Distearate; Laureth-4, Cocamidopropyl Betaine | TEGO Pearl N 300, Evonik Industries AG |
| Silicones: | |
| Amodimethicone | DC 949, Dow Corning, 100% |
| Dimethicone | ABIL 350, Evonik Industries AG, 100% |
| Dimethicone (and) Dimethiconol | DC 1503. Dow Corning |
| Quaternium-80 | ABIL Quat 3272, Evonik Industries AG, 30% |
| Silicone Quaternium-22 | ABIL T Quat 60, Evonik Industries AG, 65% |
| Dimethicone Propyl PG-Betaine | ABIL B 9950, Evonik Industries AG, 30% |
| Methoxy PEG/PPG-7/3 Aminopropyl Dimethicone | ABIL Soft AF 100, Evonik Industries AG, 100% |
| Bis-PEG/PPG-20/20 Dimethicone | ABIL B 8832, Evonik Industries AG, 100% |
| PEG/PPG-14/4 Dimethicone | ABIL B 8851, Evonik Industries AG, 95% |
| Care polymers/film formers: | |
| Polyquaternium-7 | Merquat 550, Nalco, 100% |
| Polyquaternium-10 | Polymer JR 400, Amerchol, 100% |
| Styrene/Acrylates Copolymer | Yodosol GH840, Akzo Nobel |
| Starch Hydroxypropyltrimonium Chloride | Sensomer CI-50, Nalco |
| Hydroxypropyl Guar Hydroxypropyltrimonium Chloride | Jaguar C-162, Rhodia, 100% |
| Active ingredients: | |
| Panthenol | D-Panthenol USP, BASF, 100% |
| Allantoin | Allantoin, DSM |
| Tocopheryl Acetate | Tinoderm E, BASF |
| Inulin | Inutec H25, Beneo-Remy |
| Niacinamide | Niacinamide, USP, DSM Nutrional Products, 100% |
| Creatine | TEGO Cosmo C 100, Evonik Industries AG, 100% |
| Sodium Lactate; Sodium PCA; Glycine; Fructose; Urea; Niacinamide; Inositol; Sodium Benzoate; Lactic Acid | LACTIL, Evonik Industries AG, 100% |
| Salicylic Acid | AEC Salicylic Acid, A & E Connock |
| Hydrolyzed Wheat Protein | Gluadin WLM, BASF Cognis |
| Antidandruff active ingredients: | |
| Climbazole | Crinipan AD, Haarmann & Reimer Fragrance GmbH, 100% |
| Octopirox | Octopirox, Clariant |
| Zinc Pyrithione | Zinc-Pyrion NF, WeylChem, 48% |
| Conditioners: | |
| Cetrimonium Chloride | VARISOFT 300, Evonik Industries AG, 30% |
| Palmitamidopropyltrimonium Chloride | VARISOFT PATC, Evonik Industries AG, 60% |

TABLE 85-continued

List of raw materials used:

| INCI name: | Trade name: |
|---|---|
| Surfactants: | |
| Cocamidopropyl Betaine | TEGO Betain F 50, Evonik Industries AG, 38% |
| Cocamidopropyl Betaine | TEGO Betain CK D, Evonik Industries AG, 82% |
| Capryl/Capramidopropyl Betaine | TEGO Betain 810, Evonik Industries AG, 35% |
| Undecylenamidopropyl Betaine | REWOTERIC AM B U 185, Evonik Industries AG, 30% |
| Coco-Betaine | Dehyton AB 30, BASF Cognis, 31% |
| Sodium Cocoamphoacetate | REWOTERIC AM C, Evonik Industries AG, 32% |
| Sodium Cocoamphopropionate | REWOTERIC AM KSF 40, Evonik Industries AG, 40% |
| Disodium Ricinoleamido MEA-Sulfosuccinate | REWODERM S 1333, Evonik Industries AG, 40% |
| Disodium Lauryl Sulfosuccinate | REWOPOL SB F 12 P, Evonik Industries AG, 95% |
| Disodium Laureth Sulfosuccinate | REWOPOL SB FA 30 B, Evonik Industries AG, 40% |
| Disodium PEG-5 Laurylcitrate Sulfosuccinate; Capryl/Capramidopropyl Betaine | REWOPOL SB C 55, Evonik Industries AG, 54% |
| Sodium Laureth Sulfate | Texapon NSO, BASF Cognis, 28% |
| Sodium Lauryl Sulfate | Texapon LS 35, BASF Cognis, 30% |
| Sodium Myreth Sulfate | Texapon K 14S Spez, BASF Cognis, 70% |
| Ammonium Laureth Sulfate | Standapol EA-1, BASF Cognis |
| Sodium Coco-Sulfate | Texapon HC G, BASF Cognis |
| Sodium Trideceth Sulfate | Rhodapex EST-30, Rhodia |
| Ammonium Lauryl Sulfate | Standapol A, BASF Cognis |
| MIPA-Laureth Sulfate | Zetesol 2056, Zschimmer & Schwarz GmbH |
| Hydroxysultaine | OriStar HSB, Orient Stars LLC |
| Cocamidopropyl Hydroxysultaine | Mirataine CBS, Rhodia |
| Lauryl Glucoside | Plantacare 1200 UP, BASF Cognis, 50% |
| Decyl Glucoside | Plantacare 2000 UP, BASF Cognis |
| Coco Glucoside | Plantacare 818 UP, BASF Cognis, 51% |
| Caprylyl/Capryl Glucoside | Plantacare 810 UP, BASF Cognis |
| Glyceryl Glucoside | Hydagen GG, BASF Cognis |
| Sodium Cocoyl Glutamate | Plantapon ACG HC, BASF Cognis |
| Disodium Cocoyl Glutamate | Planatpon ACG LC, BASF Cognis |
| Sodium Cocoyl Hydrolyzed Wheat Protein Glutamate | PGFAC-S, BASF Cognis |
| Lauroamphoglycinate | Miranol Ultra L-32, Rhodia |
| Sodium Cocoyl Glycinate | Hostapon SG, Clariant |
| Sodium Lauryl Sulfoacetate; Disodium Laureth Sulfosuccinate | Stepan-Mild LSB, Stepan |
| Sodium C14-16 Olefin Sulfonate | Bioterge AS-40 AOS, Stepan |
| Sodium C12-15 Pareth-15 Sulfonate | Avanel S-150 CGN, BASF |
| Sodium Anisate; Sodium Levulinate | Dermosoft 1388, Dr. Straetmans |
| Sodium Coco-Glucoside Tartrate | Eucarol AGE/ET, Cesalpina Chemicals S.P.A. |
| Sodium Lauroyl Lactylate | Dermosoft SLL, Dr. Straetmans |
| Sodium Lauroyl Sarcosinate | Crodasinic LS 30, Croda, 30% |
| Sodium Cocoyl Sarcosinate | Crodasinic CS, Croda |
| Sodium Myristoyl Sarcosinate | Crodasinic MS, Croda |
| Lauroyl Sarcosine | Crodasinic L, Croda |
| C12-14 Hydroxyalkyl Hydroxyethyl Sarcosine | Softazoline LMEB, Kawaken Fine Chemical Co. |
| Sodium Methyl Cocoyl Taurate | Adinol CT, Croda |
| Sodium Cocoyl Alaninate | Amilite ACS-12, Ajinomoto |
| Sodium Lauryl Glucose Carboxylate | Plantapon SF, BASF Cognis |
| Sodium Cocoabutteramphoacetate | Mackam 1CB, Rhodia |
| Cocamidopropyl PG-dimonium Chloride Phosphate | Arlasilk PTC, Croda |
| Sodium Lauroyl Methyl Isethionate | Iselux, Innospec Active Chemicals |
| Sodium Cocoyl Isethionate | Hostapon STCI-85 P, Clariant |
| Refatting agents/emollients: | |
| Polyglyceryl-3 Caprate | TEGOSOFT PC 31, Evonik Industries AG, 100% |
| Glyceryl Caprylate | Dermosoft GMCY, Dr. Straetmans |
| Glyceryl Stearate | TEGIN 4100 Pellets, Evonik Industries AG, 100% |
| Glyceryl Oleate | TEGIN O V, Evonik Industries AG, 100% |
| Diethylhexyl Carbonate | TEGOSOFT DEC, Evonik Industries AG, 100% |
| Caprylic/Capric Triglyceride | TEGOSOFT CT, Evonik Industries AG, 100% |
| PEG-7 Glyceryl Cocoate | TEGOSOFT GC, Evonik Industries AG, 100% |
| Sucrose Cocoate | TEGOSOFT LSE 65 K, Evonik Industries AG, 100% |
| PEG-3 Myristyl Ether | TEGOSOFT APM, Evonik Industries AG, 100% |
| Sorbitol | Sorbitol USP Powder, Lipo |
| Glycerin | Glycerol EP, vegetable, Spiga Nord, 99.7% |

TABLE 85-continued

| List of raw materials used: | |
|---|---|
| INCI name: | Trade name: |
| Hydrogenated Didecene | Satin Touch HD 2, Chevron Phillips |
| Dicaprylylether | Cetiol OE, BASF Cognis |
| Foam boosters: | |
| Hydroxypropyl Methylcellulose | TEGOCEL HPM 50, Evonik Industries AG, 100% |
| Solubilizers: | |
| PEG-40 Hydrogenated Castor Oil | TAGAT CH 40, Evonik Industries AG, 100% |
| PEG-20 Glyceryl Laurate | TAGAT L 2, Evonik Industries AG, 100% |
| Pentylene Glycol | Hydrolite-5 616751, Symrise |
| Polysorbate 20 | TEGO SML 20, Evonik Industries AG, 100% |
| Polyglyceryl-4 Caprate | TEGOSOFT PC- 41, Evonik Industries AG, 100% |

The invention claimed is:

1. A composition comprising water, at least one biosurfactant and at least one fatty acid,
wherein the fraction of the sum of all surfactants in the composition is from 1 to 30% by weight, and that the fraction of fatty acid, based on the sum of fatty acid and surfactants, is from 0.1 to 20% by weight, wherein the composition has, as biosurfactants, mono- di- or polyrhamnolipids, sophorolipids or any combination thereof, and wherein said composition further comprises at least one surfactant that is not a biosurfactant, the at least one surfactant that is not a biosurfactant selected from the group consisting of anionic surfactants, amphoteric surfactants, ampholytic surfactants, zwitterionic surfactants and combinations thereof, and wherein the fatty acid is oleic acid.

2. The composition according to claim 1, wherein the composition comprises at least one thickener.

3. The composition according to claim 2, wherein the fraction of the at least one thickener in the composition is from 0.1 to 10% by weight, based on the composition.

4. The composition according to claim 2, wherein the composition has one or more PEG-free thickeners, selected from polysaccharides, celluloses, cellulose derivatives, alkyl-modified sugar derivatives, carbomers, crosslinked polyacrylates, polyacrylamides, polyvinyl alcohol and polyvinylpyrrolidone, ethoxylated fatty acid glycerides, esters of fatty acids with polyols, fatty alcohol ethoxylates and alkyl oligoglucosides.

5. The composition according to claim 1, wherein the weight ratio of biosurfactants to surfactants which are not a biosurfactant is >1:1.

6. The composition according to claim 1, wherein the weight ratio of biosurfactants to surfactants which are not a biosurfactant is ≤1:1.

7. The composition according to claim 1, wherein the composition comprises no surfactants which have sulphates or polyethylene glycol.

8. The composition according to claim 1, wherein the composition has one or more natural dyes.

9. The composition according to claim 1, wherein the composition is free from preservatives.

10. The composition according to claim 1, wherein the composition comprises propylene glycol, urea, glycerol, essential oils, phenylethyl alcohol, ethanol or any combination thereof.

11. The composition according to claim 1, wherein the composition has perfume oils or fragrances, where the fraction of natural fragrances, based on the total number of fragrances in the perfume oils, is at least 50% by weight.

12. The composition according to claim 1, wherein the composition is a body, skin or hair treatment composition.

13. A bath additive, shower gel, shampoo, conditioner, body cleanser or impregnation solution for wet cleansing wipes or skin cleansers comprising the composition according to claim 1.

14. The composition according to claim 1, wherein the fraction of the sum of all surfactants in the composition is from 2.5 to 20% by weight.

15. The composition according to claim 1, wherein the fraction of the sum of all surfactants in the composition is from 10 to 20% by weight.

16. The composition according to claim 1, wherein the fraction of fatty acid, based on the sum of fatty acid and surfactants, is from 0.1 to 15% by weight.

17. The composition according to claim 1, wherein the fraction of fatty acid, based on the sum of fatty acid and surfactants, is from 1 to 10% by weight.

* * * * *